US007654948B2

(12) United States Patent
Kaplan et al.

(10) Patent No.: US 7,654,948 B2
(45) Date of Patent: Feb. 2, 2010

(54) AUTOMATED INSOMNIA TREATMENT SYSTEM

(75) Inventors: Richard Kaplan, Richmond Heights, OH (US); Kenneth A. Loparo, Chesterland, OH (US)

(73) Assignee: Consolidate Research of Richmond, Inc., Euclid, OH (US)

( * ) Notice: Subject to any disclaimer, the term of this patent is extended or adjusted under 35 U.S.C. 154(b) by 815 days.

(21) Appl. No.: 10/790,885

(22) Filed: Mar. 1, 2004

(65) Prior Publication Data

US 2004/0225179 A1   Nov. 11, 2004

Related U.S. Application Data

(60) Provisional application No. 60/451,055, filed on Feb. 28, 2003.

(51) Int. Cl.
*A61M 21/00* (2006.01)
(52) U.S. Cl. ..................................... 600/26
(58) Field of Classification Search ............ 600/26, 600/300, 500, 509, 544, 484, 535, 564, 575, 600/301; 379/373.01; 368/12, 107; 362/231; 340/573.1, 575; 128/204.23, 204.21, 204.26, 128/897, 898; 607/2, 46
See application file for complete search history.

(56) References Cited

U.S. PATENT DOCUMENTS

| 4,228,806 A | 10/1980 | Lidow |
| 4,354,505 A | 10/1982 | Shiga |
| 4,503,863 A * | 3/1985 | Katims ................. 600/554 |
| 4,550,736 A | 11/1985 | Broughton et al. |
| 4,617,525 A | 10/1986 | Lloyd |
| 4,776,345 A | 10/1988 | Cohen et al. |
| 5,101,831 A | 4/1992 | Koyama et al. |
| 5,154,180 A | 10/1992 | Blanchet et al. |
| 5,197,489 A | 3/1993 | Conlan |
| 5,259,390 A | 11/1993 | MacLean |
| 5,280,791 A | 1/1994 | Lavie |
| 5,299,118 A | 3/1994 | Martens et al. |
| 5,479,939 A | 1/1996 | Ogino |
| 5,520,176 A | 5/1996 | Cohen |
| 5,573,013 A * | 11/1996 | Conlan ................. 600/595 |
| 5,588,425 A | 12/1996 | Sackner et al. |
| 5,724,990 A | 3/1998 | Ogino |
| 5,732,696 A | 3/1998 | Rapoport et al. |
| 5,813,993 A | 9/1998 | Kaplan et al. |
| 5,816,247 A | 10/1998 | Maynard |
| 5,846,206 A | 12/1998 | Bader |
| 5,902,255 A | 5/1999 | Ogino |
| 5,917,415 A | 6/1999 | Atlas |

(Continued)

FOREIGN PATENT DOCUMENTS

EP           0733504 A1    5/1997

OTHER PUBLICATIONS

Riley, W. et al., "Initial Evaluation of a Computerized Behavioral Intervention for Primary Insomnia" Paper presented at the 36th Annual Convention of the Association for the Advancement of Behavior Therapy. Reno, NV (Nov. 2002).

(Continued)

*Primary Examiner*—Samuel G Gilbert
(74) *Attorney, Agent, or Firm*—Priya Sinha Cloutier; Barry Sufrin

(57) ABSTRACT

Automated behavioral methods and systems for treating insomnia that use passive means for determining wake/sleep states.

38 Claims, 9 Drawing Sheets

U.S. PATENT DOCUMENTS

| | | | |
|---|---|---|---|
| 5,928,133 | A | 7/1999 | Halyak |
| RE36,450 | E | 12/1999 | Musha |
| 5,999,846 | A | 12/1999 | Pardey et al. |
| 6,070,098 | A | 5/2000 | Moore-Ede et al. |
| 6,078,549 | A | 6/2000 | Wyatt et al. |
| 6,157,857 | A | 12/2000 | Dimpfel |
| 6,167,298 | A | 12/2000 | Levin |
| 6,171,258 | B1 | 1/2001 | Karakasoglu et al. |
| 6,239,706 | B1 | 5/2001 | Yoshiike et al. |
| 6,272,378 | B1 | 8/2001 | Baumgart-Schmitt |
| 6,317,627 | B1 | 11/2001 | Ennen et al. |
| 6,322,515 | B1 | 11/2001 | Goor et al. |
| 6,353,396 | B1 | 3/2002 | Atlas |
| 6,381,481 | B1 | 4/2002 | Levendowski et al. |
| 6,392,962 | B1 | 5/2002 | Wyatt |
| 6,468,234 | B1 | 10/2002 | Van der Loos et al. |
| 6,496,724 | B1 | 12/2002 | Levendowski et al. |
| 6,497,658 | B2 | 12/2002 | Roizen et al. |
| 6,511,424 | B1 | 1/2003 | Moore-Ede et al. |
| 6,575,902 | B1 | 6/2003 | Burton |
| 6,625,485 | B2 | 9/2003 | Levendowski et al. |
| 2001/0028309 | A1 | 10/2001 | Torch |
| 2001/0031930 | A1 | 10/2001 | Roizen et al. |
| 2002/0005784 | A1 | 1/2002 | Balkin et al. |
| 2002/0029005 | A1 | 3/2002 | Levendowski et al. |
| 2002/0067273 | A1* | 6/2002 | Jaques et al. ............. 340/573.4 |
| 2002/0082513 | A1 | 6/2002 | Ennen et al. |
| 2002/0183644 | A1 | 12/2002 | Levendowski et al. |
| 2003/0181821 | A1 | 9/2003 | Greenwald et al. |

OTHER PUBLICATIONS

"Advanced Brain Monitoring, LLC. Announces News Research Program to Identify Indices of Alertness" *PR Newswire* (Aug. 10, 1999).
"Interpreting the Brain", "Technologies, Products, and Market Applications—EEG", "Drowsiness Monitoring Device", "Patented Sensor Headset" Advanced Brain Monitoring, Inc. Home p. www.b-alert.com (2002).
Sadeh, A. et al., "The Role of Actigraphy in the Evaluation of Sleep Disorders" *Sleep* (May 1995); 18(4):288-302.
Dirckx, J., "Wake Me When It's Over: Sleep and Its Disorders" *Perspectives* (Spring 2000); 28-35.
Xin, P. et al., "Habituation of Sleep to Road Traffic Noise Assessed by Polygraphy and Rating Scale" *Journal of Occupational Health*(2000);42:20-26.
Eiken, T., "Equipment and Facility Considerations: Establishing a Sleep (May 1999); 35-38. Disorders Center" *AARC Times*(May 1999); 35-38.
Craig, C., "Introduction to Sleep Disorders" Healthylnfo.com www.healthyinfo.com (2002).
Portas, C. et al., "Auditory Processing Across the Sleep-Wake Cycle: Simultaneous EEG and fMRI Monitoring in Humans" *Neuron* (Dec. 2000); 28(3):991-999.
*Principles and Practices of Sleep Medicine, Third Edition*, Eds. Kryger. M. et al., Philadelphia, PA: W.B. Saunders Company (2000).
Bootzin, R., *Behavioral Modification and Therapy—An Introduction*, Cambridge, MA: Winthrop Publishers, Inc. (1975).
Lacks, P., *Behavioral Treatment for Persistent Insomnia*, Pergamon Books, Inc. (1987).
Yang, C., "Insomnia" *American Academy of Neurology—Continuum* 8(6), Lippincott Williams & Wilkins, American Academy of Neurology (2002).
"Table DP-1: Profile of General Demographic Characteristics for the United States: 2000" *United States Census 2000*, U.S. Census Bureau.
Bootzin, R. et al., "Stimulus Control" *Treatment of Late-life Insomnia*, Eds. Lichstein, K. et al., Thousand Oaks, CA: Sage Publications (2000).
Bootzin, R. et al. "Sleep Disorders" *Comprehensive Handbook of Psychopathology, Third Edition*, Eds. Sutker P. et al., New York: Kluwer Academic/Plenum Publishers (2001).
Bootzin, R. et al., "Behavioral Treatments for Insomnia" *Progress in Behavior Modification, vol. 6*, Eds. Hersen, M. et al, New York, NY: Academic Press Inc. (1978).
Dorsey, C. et al., "Subjective and Psychophysiologic Insomnia: An Examination of Sleep Tendency and Personality" *Biological Psychiatry*(Jan. 15, 1997); 41(2):209-216.
Espie, C. et al., "Substituting Behavioural Treatment for Drugs in the Treatment of Insomnia: An Exploratory Study" *Journal of Behavior Therapy & Experimental Psychiatry*(Mar. 1988); 19(1):51-56.
Hauri, P., "Treating Psychophysiologic Insomnia with Biofeedback" *Archives of General Psychiatry* (Jul. 1981); 38(7):752-758.
Hauri, P., "Consulting About Insomnia: A Method and Some Preliminary Data" *Sleep* (Jun. 1993); 16(4):344-350.
Morin, C. et al, "Nonpharmacologic Treatment of Chronic Insomnia: An American Academy of Sleep Medicine Review" *Sleep* (Dec. 1999); 22(8):1134-1156.
Engle-Friedman, M. et al, "An Evaluation of Behavioral Treatments for Insomnia in the Older Adult" *Journal of Clinical Psychology* (Jan. 1992); 48(1):77-90.
Bootzin, R. et al., "Nonpharmacologic Treatments of Insomnia" *Journal of Clinical Psychiatry* (Jun. 1992); 53(Supp.):37-41.
Sloan, E. et al., "The Nuts and Bolts of Behavioral Therapy for Insomnia" *Journal of Psychosomatic Research*(1993); 37(Supp. 1):19-37.
"2002 'Sleep in America' Poll" (Mar. 2002), National Sleep Foundation.
Adachi, Y., "Behavioral Treatment for Chronic Insomnia" *Seishin shinkeigaku zasshi = Psychiatria et neurologia Japonica*(2002); 104(6):513-528.
Hajak, G. et al., "As needed' Pharmacotherapy Combined with Stimulus Insomnia—Assessment of a Novel Intervention Strategy in a Primary Care Setting" *Annals of Clinical Psychiatry: Official Journal of the American Academy of Clinical Psychiatrists* (Mar. 2002); 14(1):1-7.
Morin, C. et al., "Behavioral and Pharmacological Therapies for Late-life Insomnia: A Randomized Controlled Trial" *JAMA: The Journal of the American Medical Association* (Mar. 17, 1999); 281(11):991-999.
Vvincent, N. et al., "Treatment Preference and Patient Satisfaction in Chronic Insomnia" *Sleep* (Jun. 15, 2001); 24(4):411-417.
Edinger, J. et al, "Cognitive Behavioral Therapy for Treatment of Chronic Primary Insomnia: A Randomized Controlled Trial" *JAMA: The Journal of the American Medical Association* (Apr. 11, 2001); 285(14):1856-1864.
Morin, C. "Nonpharmacologic Treatment of Chronic Insomnia An American Academy of Sleep Medicine Review." *sleep*(Dec. 15, 1999); 22(8):1128-1133.
Chesson, A. et al., "Practice Parameters for the Nonpharmacologic Treatment of Chronic Insomnia An American Academy of Sleep Medicine Report. Standards of Practice Committee of the American Academy of Sleep Medicine." *Sleep*(Dec. 15, 1999); 22(8):1128-1133.
KirkWood, C. "Management of Insomnia" *Journal of the American Pharmaceutical Association(Washington, DC: 1996)*(Sep.-Oct. 1999); 39(5):688-696; Quiz 713-714.
"Practice Parameters for the Use of Polysomnography in the Evaluation of Insomnia. Standards of Practive Committe of the American Sleep Disorders Association," *Sleep* (Jan. 1995); 18(1):55-57.
Morin, C. "Cognitive-behavior Therapy for Late-life Insomnia" *Journal of Consulting and Clinical Psychology* (Feb. 1993); 61(1):137-146.
Edinger, J. et al., "A Cognitive-behavioral Therapy for Sleep-maintenance Insomnia in Older Adults"*Psychology and Aging* (Jun. 1992); 7(2):282-289.
Friedman, L. et al., "A Preliminary Study Comparing Sleep Restriction and Relaxation Treatments for Insomnia in Older Adults" *Journal of Gerontology* (Jan. 1991); 46(1):P1-8.
Yang, Chien-Ming, "Insomnia," *American Academy of Neurology—Continuum*, vol. 8(6), Lippincott Wiliams & Wilkins, American Academy of Neurology, p. 106-118, (2002).

* cited by examiner

AUTOMATED INSOMNIA TREATMENT SYSTEM

CROSS-REFERENCE TO RELATED PATENT APPLICATIONS

This application claims the benefit of U.S. Provisional Patent Application No. 60/451,055 filed Feb. 28, 2003.

FIELD OF THE INVENTION

This invention is directed generally to helping people suffering from insomnia and, more particularly, to highly effective automated systems for treating insomnia that use passive methods of determining wake/sleep states.

BACKGROUND

Insomnia is a complaint that sleep is difficult to initiate or maintain, or that it is not refreshing or restorative. A person that suffers from insomnia has difficulty falling asleep or staying asleep, or wakes too early. As a consequence, insomnia sufferers begin to dread not only each night of sleeplessness but also the fatigue, mental clouding, and irritability of the coming day.

Insomnia is a widespread problem. For example, a study conducted in the United States revealed that more than 50% of the respondents reported having experienced at least one of the following symptoms of insomnia at least a few nights a week: difficulty falling asleep, waking often during the night, waking up too early and not being able to get back to sleep, and waking up feeling unrefreshed. In fact, 35% of the respondents said that they experienced at least one of these four symptoms of insomnia every night or almost every night. Extrapolating these study statistics to the United States Census data at the time the study was conducted suggests that over 120 million U.S. adults experience at least one of the four symptoms of insomnia at least a few nights every week. Of this 120 million, over 70 million experience these symptoms every night or almost every night. The direct economic costs of insomnia in the U.S. are estimated at close to $14 billion annually. The amount spent on over the counter medications and "alternative" treatments such as herbal remedies may double this estimate.

Nonpharmacologic behavioral therapies have achieved significant success in treating insomnia. Behavioral therapies have many advantages over pharmacologic therapies, including:

No risk of tolerance, dependence or side effects.
Correcting core behavior instead of treating symptoms.
Documented safety and effectiveness.

There are a number of nonpharmacologic behavioral therapies that have been found to be effective for the treatment of insomnia. Those that have been most extensively evaluated are stimulus control therapy, sleep restriction therapy, relaxation training and paradoxical intention. Among these therapies, no techniques have been found to be more effective than stimulus control therapy.

Stimulus control therapy is based on the premise that insomnia is a conditioned response to temporal (bedtime) and environmental (bed/bedroom) cues that are usually associated with sleep. Accordingly, the main objective of stimulus control therapy is to reassociate the bed and bedroom with rapid sleep onset by curtailing overt and covert sleep incompatible activities that serve as cues for staying awake and by enforcing a consistent wake and sleep schedule. Stimulus control therapy may be characterized as consisting of the following instructional procedures:

1. Use the bed and bedroom only for sleep (sexual activity is the only exception to this rule);
2. When you get into bed, turn out the lights with the intention of going right to sleep;
3. If you find yourself unable to fall asleep within a brief period of time (e.g. 15 to 20 minutes), then get out of bed and leave the bedroom. Stay up as long as you wish and then return to the bedroom when ready to sleep;
4. If you still cannot fall asleep, repeat step 3. Do this as often as is necessary throughout the night;
5. Maintain a regular wake time in the morning regardless of sleep duration the previous night, and
6. Avoid daytime napping.

Another nonpharmacologic behavioral approach to treating insomnia, sleep restriction therapy, consists of curtailing the amount of time spent in bed to more nearly match the subjective amount of time asleep. For example, if a person reports sleeping an average of 5 hours per night out of 8 hours spent in bed, the initial prescribed sleep window (i.e., from bedtime to arising time) would be 5 hours. Subsequently, the allowable time in bed is increased by 15-20 minutes for a given week when sleep efficiency (ratio of total sleep time to the total time spent in bed) exceeds 0.9, decreased by the same amount of time when sleep efficiency is lower than 0.8, and kept stable when sleep efficiency falls between 0.8 and 0.9. Adjustments are made periodically (usually on a weekly basis) until the desired sleep duration is achieved. Sleep restriction therapy promotes a more rapid sleep onset, higher sleep efficiency, and less inter-night variability. Also, to prevent excessive daytime sleepiness when implementing sleep restriction therapy, it is generally recommended that time in bed should not be less than 5 hours per night.

Those behavioral techniques for treating insomnia that require self-assessment of sleep parameters (such as sleep onset latency, total time asleep, total time awake after sleep onset, sleep efficiency, etc.) could be significantly enhanced if the burden of consciously keeping track of sleep parameters is relegated to an automated system. For example, with current approaches to sleep restriction therapy, the patient is required to note the amount of sleep achieved each night and manually calculate their average time asleep and average sleep efficiency for each week. Given the tendency for a person suffering from insomnia to grossly underestimate their time asleep, they could unnecessarily begin the program with an overly restrictive sleep schedule, thereby reducing compliance by making the regimen less tolerable. Furthermore, the patient would need to continually reevaluate their sleep parameters and adjust their sleep schedule as appropriate.

Central to the automation of behavioral therapies for insomnia is the determination of sleep parameters. The determination of sleep parameters requires wake/sleep determination, that is, a determination as to whether the subject is awake or asleep, as those terms are understood by those skilled in the art. The known techniques for determining wake/sleep states fall into two broad categories, determined from the perspective of the subject using the device, either active or passive. A device that relies upon the subject to perform an action in order to determine whether they are awake or asleep is considered an active device. An active device could require, for example, that the subject respond to an audio tone with a button press or could require holding down the plunger of a dead mans switch in order to infer/determine whether the subject is awake or asleep at any given instant in time. By contrast, a passive device would require no action on the part of the subject to determine whether they are awake or asleep.

A passive device, for example, could use electroencephalographic (EEG) signals to indicate the wake or sleep state, and this would not require any action on the part of the subject in making this determination.

There are advantages and disadvantages to both categories of devices. Probably the single biggest advantage of the active devices over passive is their relative simplicity. For example, monitoring the contact status of a dead mans switch (an active device) is much simpler and more straightforward than trying to determine changes in the wake/sleep state using EEG analysis (a passive device).

In 2002, Riley, W., et al., in an abstract entitled *Initial Evaluation of a Computerized Behavioral Intervention for Primary Insomnia* from the 36$^{th}$ Annual Convention of the Association for the Advancement of Behavior Therapy in Reno, Nev., described a behavioral therapy for insomnia that required wake/sleep state information. Their approach used an active device that produced a low volume auditory beep every 10 minutes to which the subject was required to respond. This presentation of the beep and the subsequent response (or lack thereof) was used to determine the wake/sleep state of the subject. Active methods of wake/sleep determination, such as this, are not truly automatic and have many drawbacks, including the following:

(1) A continuous presentation of stimuli (beeps) can produce undue task loading of the subject. If the subject is tasked with responding to very frequent stimuli, then the device itself can interfere with the process of falling asleep. On the contrary, if the stimuli are presented too infrequently, then the time localization of the wake/sleep determination could become too inaccurate because of the temporal granularity. Long time intervals between successive stimuli provide an opportunity for the subject to fall asleep but are at odds with the device's need for current information about the subject's wake/sleep status. For example, with the presentation of successive stimuli every 10 minutes, the device does not know what happened during the intervening time; the subject could have fallen asleep and awoken during the interval, etc. This could negatively impact the implementation of a behavioral therapy.

(2) The stimuli used in the active device of Riley et al. has the potential of being missed by the subject if it is of low amplitude, or it could wake the subject if the amplitude is too high. Alternatively, an active device employing a small amplitude vibratory stimulus could be missed, and a large amplitude vibratory stimulus could wake the subject. The same drawbacks apply to other types of stimuli used in active devices.

(3) When using an active device, the subject will be at a more heightened level of vigilance and may also be encumbered with having to perform a task. As a result, the subject cannot simply relax in bed and passively rely on the device. Active devices can be especially detrimental to insomniacs because sleep time for insomniacs is more stressful than for people without sleep problems. While tasks required of anyone trying to fall asleep would have a negative impact on sleep, this is especially so in insomniacs. Even a task as simple as depressing the plunger of a dead mans switch would necessitate a higher level of vigilance (i.e. making sure they continue holding down the switch) during a time when they should be relaxing and drifting off to sleep.

(4) Some active methods could awaken a bed partner, particularly if they use visual or audible stimuli.

(5) Methods that employ switch contacts suffer from the inability to reengage automatically when the subject wakes. Because of this, they can only detect the first episode of sleep onset. A person suffering with insomnia could also have trouble falling back to sleep after waking during the night, or, perhaps they may simply have trouble staying asleep. A dead mans switch, for example, would have to be reengaged by the subject in order for the device to redetermine the next period of sleep onset after waking. These methods would be extremely cumbersome to use for most normal sleepers and would be especially difficult for someone with highly disrupted sleep.

Active wake/sleep determination methods have also been described for other applications including the following:

MacLean U.S. Pat. No. 5,259,390 describes a hand mounted vibrating stimulus-response device to monitor sleep behavior. This device is intended for in-home prescreening of sleep before a full polysomnogram is given. It determines wake and sleep states by requiring the subject to press the response button each time they feel the vibratory stimulus.

Wyatt et al. U.S. Pat. No. 6,078,549 is directed to a sleep pattern timer using a plurality of switches to record parameters such as time before sleep onset, sleep time, etc. This device is used to assist in the diagnosis and treatment of sleep disorders by requiring the subject to hold switch(es) in a closed position and then release when the subject falls asleep.

Wyatt U.S. Pat. No. 6,392,962 entails a method of providing information to aid in the treatment of sleep disorders that would otherwise be difficult because of an insomniac's underestimation of total sleep time and/or overestimation of the time necessary to fall asleep. The apparatus, which includes a wrist-mounted timer with a hand mounted actuator, stops timing when the insomniac falls asleep and this disengages contact with the actuator. It is intended for wake/sleep determination (at sleep onset), and to correct an insomniac's overestimation of sleep latency and underestimation of total sleep and sleep efficiency.

To the knowledge of the present inventors, passive methods of determining wake/sleep have not been used or suggested to automate the implementation of behavioral sleep therapies. Such methods can determine the wake/sleep state of the subject without the need of any action on the part of the subject or the presentation of response inducing stimuli. Examples of devices that may be used to passively determine wake/sleep states (but do not teach or suggest automated behavioral therapy for insomnia) include:

1) Blanchet et al. U.S. Pat. No. 5,154,180 (system to automatically determine sleep stage using an EEG);
2) Conlan U.S. Pat. No. 5,197,489 (system that can detect wake and sleep using an activity (or movement) monitor (actigraphy));
3) Lavie U.S. Pat. No. 5,280,791 (system that can determine the sleep state of a person by analyzing cardiac EKG R-R intervals);
4) Ogino U.S. Pat. No. 5,479,939 (device that can be used to determine between wake and sleep through a non-contact body movement sensor in bed);
5) Conlan U.S. Pat. No. 5,573,013 (system that can detect wake and sleep using an activity monitor (actigraphy));
6) Sackner et al. U.S. Pat. No. 5,588,425 (system that can be used to discriminate between sleep and wake in a monitored subject based on systolic upstroke times in a pulse oximetry waveform);
7) Ogino U.S. Pat. No. 5,724,990 (device that can be used to distinguish between wake and sleep through a non-contact body movement sensor in a bed or seat);
8) Rapoport et al. U.S. Pat. No. 5,732,696 (system that uses multiple physiological signals (EEG, EMG and EOG) to score sleep);

9) Kaplan et al. U.S. Pat. No. 5,813,993 (to the present inventors) (system that tracks the state of a subject along a continuum of alertness, drowsiness, sleep, unconsciousness or anesthesia from a single channel of spontaneous EEG);

10) Bader U.S. Pat. No. 5,846,206 (system that estimates a person's wakefulness using a stationary pressure sensor in contact with that person's body);

11) Ogino U.S. Pat. No. 5,902,255 (device that can be used to distinguish between wake and sleep through a non-contact body movement sensor in a bed or seat);

12) Halyak U.S. Pat. No. 5,928,133 (device for waking a person within a preset time range when the subject is, for all intents and purposes, already awake, using general technologies such as the use of "physiological monitoring means" or "measured electrical resistance" or "monitoring a bodily electrical property");

13) Pardey et al. U.S. Pat. No. 5,999,846 ("insomnia or vigilance monitor" using an electrical signal from a subject (EEG or otherwise) over a period of epochs, method for assigning a sleep stage type to each epoch using a neural network to determine wake and sleep in order to generate a hypnogram, a method for analyzing the hypnogram to generate a summary index of sleep quality and a method to display summary index of sleep quality based on the hypnogram;

14) Dimpfel U.S. Pat. No. 6,157,857 (system for sleep staging using the EEG);

15) Baumgart-Schmitt U.S. Pat. No. 6,272,378 (system to automatically generate a sleep stage classification using a single frontal EEG derivation using a device that stores a set of features (FFT based) from the incoming data (as a method of compression) and then analyzes these features to determine sleep stages using a neural network);

16) Goor et al U.S. Pat. No. 6,322,515 (system that is capable of determining sleep and wake by monitoring and detecting changes in peripheral arterial tone);

17) Van der Loos et al. U.S. Pat. No. 6,468,234 (sensor sheet that is laid on top of a conventional mattress for measuring the sleep quality of a subject); and 18) Levendowski et al. U.S. Pat. Nos. 6,496,724, 6,625,485 and U.S. Publication No. 2002/0183644 (a system that quantifies the EEG along an alertness continuum).

Any of the above passive methods/devices for wake/sleep determination can be used in the practice of the present invention.

SUMMARY OF THE INVENTION

The present invention comprises a system for behavioral insomnia treatment therapies that require knowledge of sleep parameters in their implementation. This system uses passive wake/sleep determination to achieve a truly automated system that does not require action on the part of the subject being treated to produce information indicative of the subject's wake/sleep state.

Thus, the present automated method entails choosing a behavioral therapy that utilizes information indicative of the subject's wake/sleep state, providing passive wake/sleep determination means to produce information indicative of the wake/sleep state and implementing the steps of the behavioral therapy utilizing the wake/sleep information as appropriate.

While any behavioral therapy that utilizes information indicative of the subject's wake/sleep state may be used, stimulus control therapy, sleep restriction therapy, and combinations of the two are preferred in the practice of the present invention. Also, while any passive wake/sleep determination means may be used, it is presently preferred that the determination means be chosen from among EEG, EKG, EOG, actigraphy, body movement, galvanic skin response, respiratory changes, eye movements, and combinations of two or more of these passive wake/sleep determination means. EEG is the presently preferred sleep determination means.

Drug therapy may be used in conjunction with the behavioral insomnia treatment therapy implemented according to the automated method of the invention. Also, active means for determining the wake/sleep state may be used to supplement the passive wake/sleep determination means.

In one important embodiment, a system according to the present invention would include: 1) means for powering on the system, 2) means for passive wake/sleep determination, 3) means for determining whether the subject should get out of bed according to the appropriate behavioral therapy rules, and 4) means for alerting the subject to leave the bed if a determination is made according to the behavioral therapy rules that the user should get out of the bed.

In another important embodiment of the invention, a system is provided for treating subjects suffering from insomnia including: 1) means for powering on the system, 2) means for determining whether the system is in a training mode, 3) means for passive wake/sleep determination, 4) means for determining whether the subject has completed their sleep period, and if so, computing overnight sleep statistics, 5) means for calculating sleep restriction therapy parameters based on previously-acquired sleep data, and 7) means for displaying the calculated sleep restriction therapy program parameters for the upcoming sleep session.

DETAILED DESCRIPTION OF THE PREFERRED EMBODIMENTS

Figure 1:
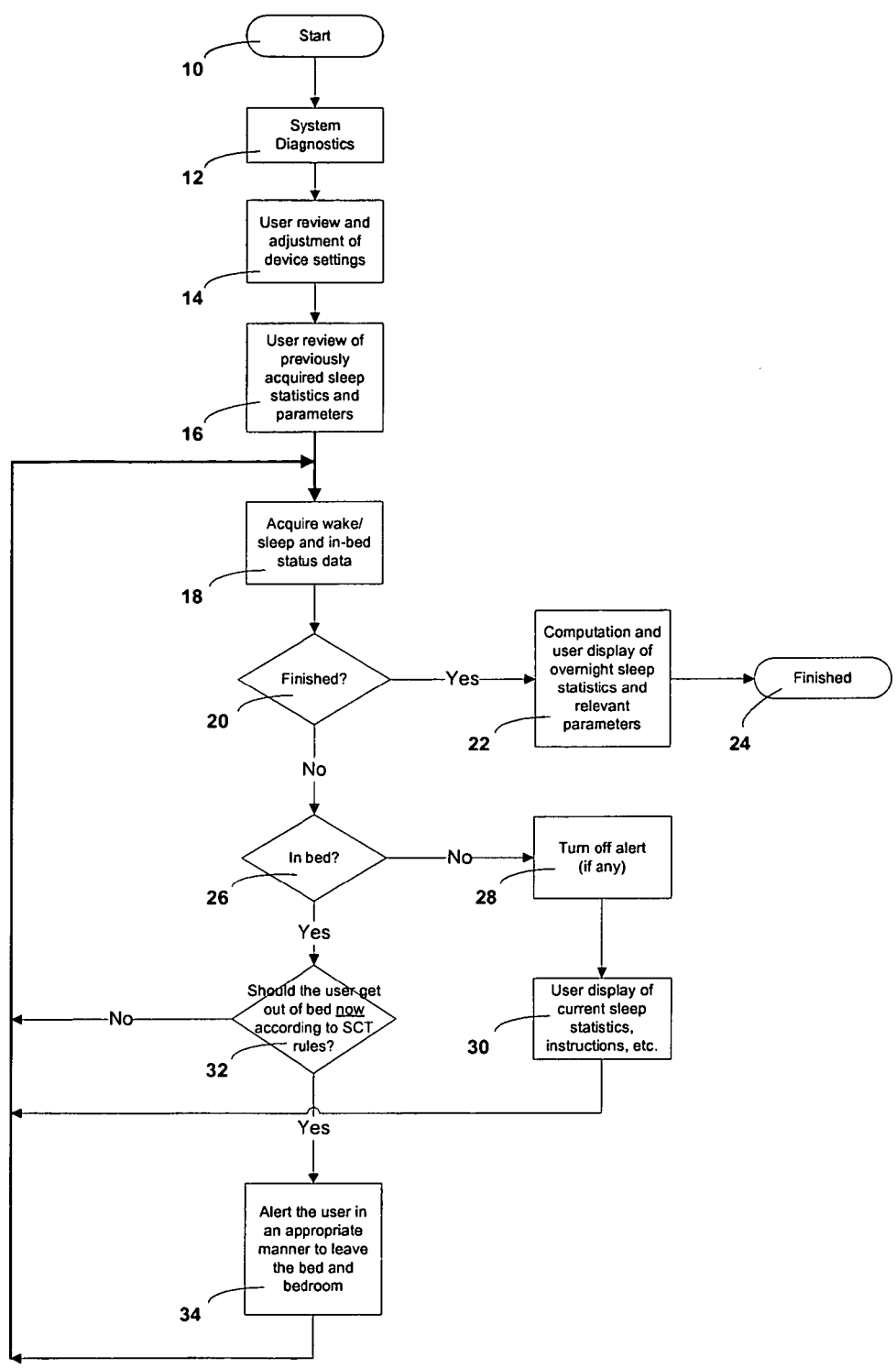
FIG. 1 is a flowchart presenting a high level overview of an automated implementation of stimulus control therapy in accordance with the present invention.

The present invention employs passive wake/sleep determination means as part of an automated system for those implementing behavioral therapies for treating insomnia that require knowledge of sleep parameters in their implementation. Such behavioral therapies include, for example, stimulus control therapy, sleep restriction therapy and combinations thereof.

In order to implement those behavioral therapies for treating insomnia that require knowledge of sleep parameters in their implementation, it is necessary to determine if the patient is awake or asleep at regular intervals of time. Highly accurate wake/sleep determination is desirable in order to achieve the best therapeutic results. Furthermore, being able to accurately determine the wake/sleep state continuously or at very closely spaced time intervals is preferred over a coarse sampling of time. This may be achieved using passive wake/sleep determination means that use, for example, EEG, EKG, EOG, actigraphy, body movement, galvanic skin response, respiratory changes, eye movements, or determination means that combine two or more of these modalities. Also, while the focus of the present invention is on the automation of nonpharmacologic behavioral treatments of insomnia, this inventive system may be employed where drug therapies are used in conjunction with behavioral therapies for the treatment of insomnia. Finally, while passive techniques and devices for determining the wake/sleep state are always at the heart of the practice of the present system, active techniques and devices for determining the wake/sleep state may be used in a supplementary way at steps in the system where interference with sleep is not at issue.

EEG based wake/sleep state determination means are currently preferred in the practice of the invention. Such devices passively monitor the state of the subject (awake or asleep). Because sleep originates in the brain and is controlled by the brain, the EEG signal provides a good information source for wake/sleep state determination.

Devices that determine wake and sleep by analyzing the information from movement/motion sensors (actigraphy, etc.) may also be used to passively detect wake/sleep states. For insomniacs that have very disrupted and restless sleep, such devices could underestimate the time asleep. Another type of insomniac may spend hours in bed lying very still in an attempt to fall asleep. In this situation, movement/motion based monitors may overestimate the time asleep. Such monitors may be obtained, for example, from Cambridge Neurotechnology Ltd. (United Kingdom) (Actiwatch), Mini Mitter Co., Inc. (Bend, Oreg.) (Mini Mitter), and Ambulatory Monitoring, Inc. (Ardsley, N.Y.), which sells a number of activity monitoring products.

The implementation of stimulus control therapy and sleep restriction therapy requires following a set of guidelines and instructions. These guidelines and instructions can be represented in the form of a flowchart for each of the techniques. The following FIGS. 1, 2A-2E, and 3 demonstrate how each technique could be implemented in an automated system in accordance with the present invention.

Application to Stimulus Control

As explained earlier, stimulus control is a behavioral therapy designed to help the insomniac establish consistent wake and sleep patterns, establish the bed and bedroom as cues for sleep, and reduce the insomniac's association with activities that might interfere with sleep. Stimulus control has been found to be a particularly effective intervention for both sleep onset insomnia and sleep maintenance insomnia. The automated implementation of stimulus control as used in the present invention is based upon the following rules:

Standing Rules (Always Running)
 1. Never alert a subject while they are asleep.
 2. After any sleep of less than 10 contiguous minutes, at least 2 contiguous epochs of wake are needed before an alert is permitted.
 3. After any sleep of at least 10 contiguous minutes, alert the subject according to the 15 Minute Rule (see below).

Special Rules (Only Running During Sleep Onset)
 1. If there is no sleep of at least 5 contiguous minutes within the first 20 minutes of trying to fall asleep, then alert at 20 minutes elapsed time.
 2. If there is a contiguous sleep period contained entirely within the first 20 minute period of trying to fall asleep, that is greater than or equal to 5 minutes, but less than 10 minutes, then inhibit alert for an additional 10 minutes.

15 Minute Rule
 1. Use a sliding window to examine the past 15 minutes of sleep. If it has been determined that the subject was awake for at least 14 of the past 15 minutes, then alert.

FIG. 1, a flowchart presenting a high level overview of an automated implementation of stimulus control therapy in accordance with the present invention, is discussed immediately below. Details and enhancements to the system overview are then presented in connection with the discussion of the flowcharts of FIGS. 2A-2E.

The system starts with power-on (or connection of EEG electrodes) at 10. The system completes a diagnostic procedure 12 that may include: hardware, software, power, electrode/sensor status, etc. Errors and warnings should be handled as appropriate. Following diagnostics, there should be an opportunity for the user to make adjustments to system settings 14. On the first use of the device, these settings may be displayed for review by default. On subsequent use of the device, this menu may be optionally displayed or called up by the user. These settings will include such items as setting the current time, age, sleep goals, alert preferences, (audible, tactile or both), language, display preferences, setup preferences, backlight preferences, use of abbreviated messages, use of verbose messages, etc.

Each time the device is started (or the user is connected, etc.) it may display individual night or summary statistics and allow the user to review these as desired 16. Progress trends, etc. may also be displayed at 16. This all falls under the category of user feedback.

The system will need to acquire sleep related parameters. For this implementation, the system acquires wake/sleep data, in-bed status (either derived manually or using automatic means) and the time (or elapsed time) for each at 18. These observations could be made every 30 seconds.

When the user is finished using the system, the recording and computation of sleep related parameters stops at 20. The system will know that the recording is finished either by the user manually indicating this to the device or when the electrodes/sensors are disconnected. When the data collection is completed, the system will display to the user at 22 the most recent overnight sleep statistics and other relevant parameters. It would report figures that would be of interest to the user, such as: time to sleep onset, total time in bed, total time spent asleep, total time spent awake, total time spent awake after sleep onset, number of awakenings, etc. The system then finishes at 24. If the user, however, is not finished at 20, then the system checks the in-bed status at 26. If the user is not in bed, then the alerts are turned off (if any are currently on) at 28 and an informational display is presented at 30. Recording and computation of sleep related parameters continues while the user is out of bed (18). An information display 30 may display to the user their current sleep statistics for this sleep session and could provide specific out of bed instructions (such as: do not nap, go back to bed only when ready to sleep, etc.)

If the user was in bed at step 26, then the system reviews their current sleep status and sleep history at 32 to determine if the rules of stimulus control therapy suggest that the user should get out of bed. (See the stimulus control therapy rules for more specific information.) If, for example, the user has been awake for the past 15 minutes after being asleep, then the rules for stimulus control therapy would suggest that the user get out of bed and leave the bedroom. The device would signal an alert to the user (according to their device settings) and display a message that they should leave the bed and bedroom, and return to bed only when ready to try to sleep again. If the stimulus control therapy rules did not suggest that the user get out of bed at 32, then the system returns to 18 and continues monitoring. The data collected each night (which could be collected at step 18) would look similar to:

TABLE 1

Sleep History

| | | | | Time | | | | |
|---|---|---|---|---|---|---|---|---|
| | 0 | 30 | 60 | 90 | ... | 25200 | 25230 | 26000 |
| Awake? | 1 | 1 | 1 | 1 | ... | 0 | 0 | 0 |
| In-bed? | 0 | 0 | 0 | 1 | ... | 1 | 1 | 1 |

Time: elapsed time in seconds
Awake: determined periodically by the wake/sleep determination means
In-bed: determined by the in-bed sensor or user indicated The memory required to store the data of Table 1 is minimal. If we assume a new set of values every 30 seconds, and use a 4 byte long integer to store the time and a 1 byte number to store the awake and in-bed results, this would result in 12 bytes/minute. At this rate, 1 megabyte of memory or other storage device could hold over 180 nights of sleep history data, or over 60 days of continuous recording.

In the above example, the user started awake and out of bed and finished asleep and in-bed. As the system runs during the sleep period, new sleep history values are added to the table (either in memory or in a storage device). Any of the behavioral therapies implemented using the present invention, as well as several of the sleep hygiene rules, can make use of the sleep history information.

The above sleep history data is sufficient to implement the stimulus control therapy program and allow the user to track their progress toward helping their symptoms of insomnia.

Figure 2A:
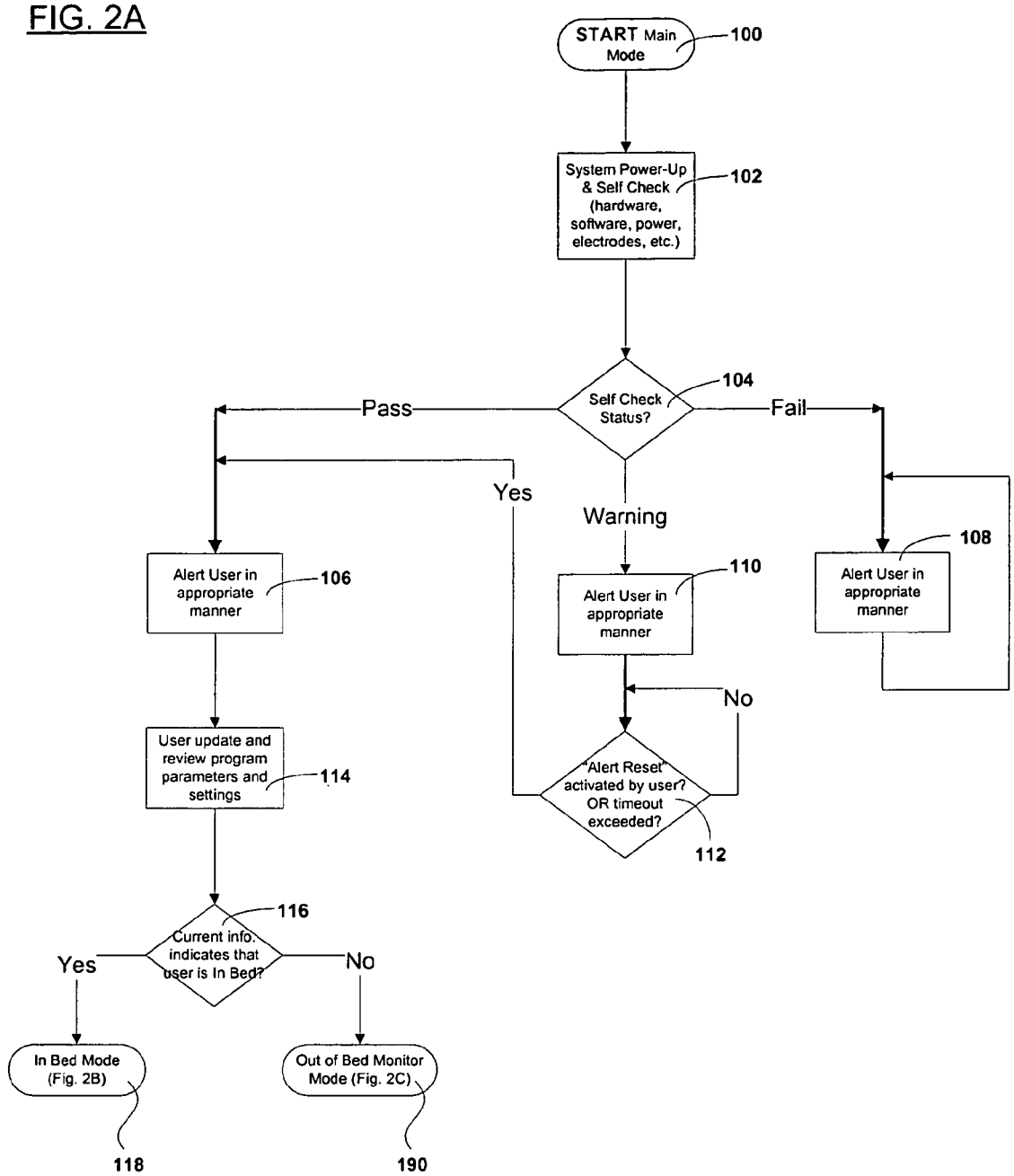
FIGS. 2A-2E are flowcharts including details of the automated implementation of stimulus control therapy in accordance with the present invention.
Figure 2B:
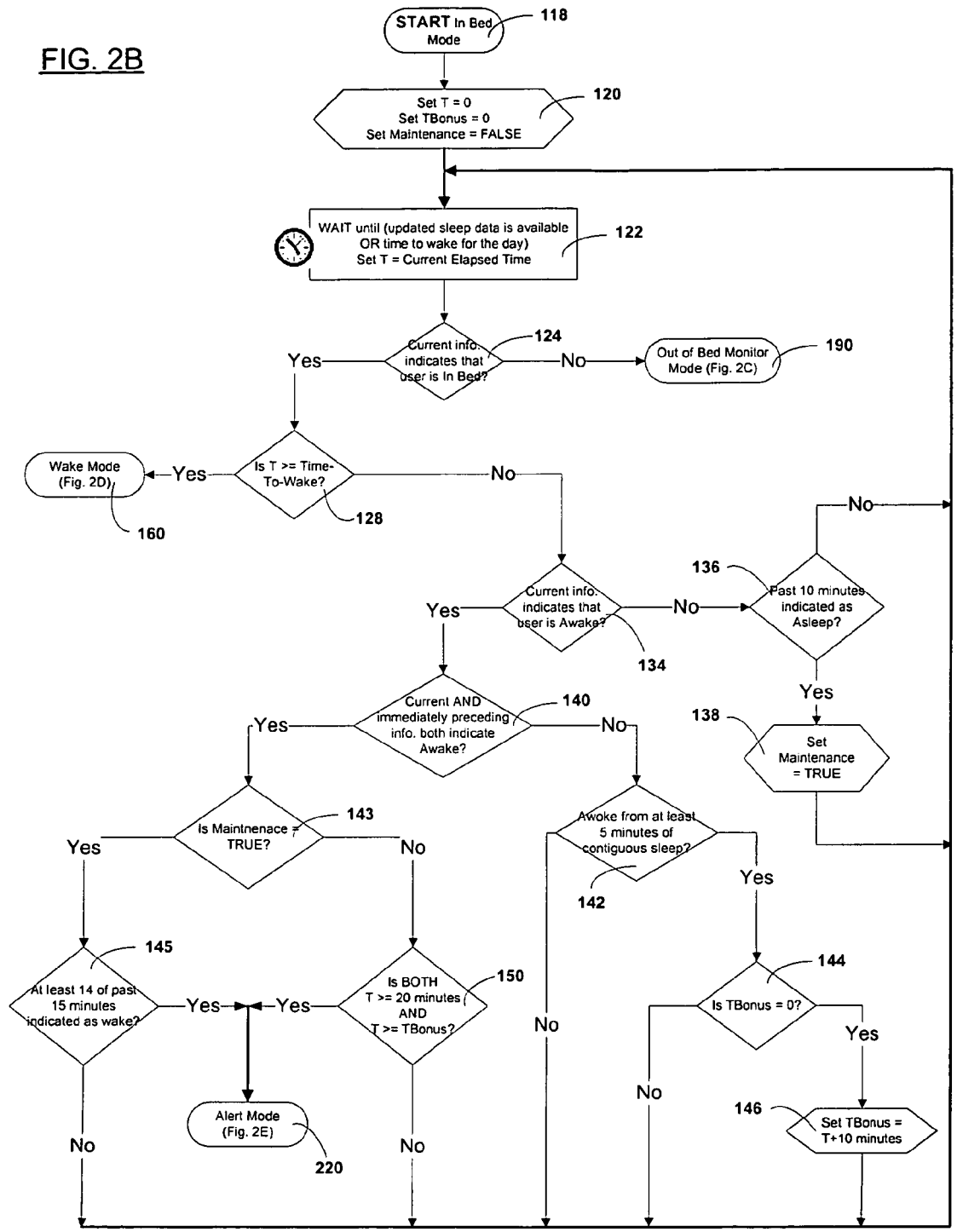

Turning now to the flow diagram of FIG. 2A, an example implementation of a stimulus control system in accordance with the present invention is shown. Beginning with START 100, system power up and self-check 102 is enabled. The self-check includes standard diagnostics for the hardware and software, power levels, sensor checks (e.g., for EEG electrodes, or check as to whether the electrodes are connected to the system and the electrode impedance is within acceptable ranges), etc. Although not detailed in the flow diagram, the system should continuously or periodically check for valid sensor signals and the integrity of the sensor connections.

The status of the self-check is determined (pass, fail or warning) and the system branches to pass, fail or warning at status check 104. If the self-check passes, the system proceeds to step 106. If the self-check finds a condition in which the device should not be operated (i.e. batteries too low to operate, hardware malfunction, etc.), then a failed status exists and the system proceeds to 108. If the self-check detects a warning condition (batteries starting to get low, etc.), then the system alerts the user at 110 and either times out or resets at 112.

Depending on user preferences, the warning condition alert may be any one or more of a text display of the warning condition, a text display of instructions or information, activation of the display backlight, a blinking light, an audible indication, a tactile indication, a synthesized or recorded voice, a low level electrical stimulus or even an aroma generated by an appropriate device. We refer to these alerts (as well as any other appropriate alerts) as "the Alert Set." The user may acknowledge the alert by issuing an Alert Reset at 112, most likely by a button press, although this condition could optionally time out after a preset length of time, i.e. 30 seconds. In either case, the device would continue to 106. Also, if an error condition is generated during the self-check 102/104, then the system will produce one or more appropriate alerts from the Alert Set. This condition would not allow the device to be used until the error condition is remedied and the device is restarted, i.e. by cycling the power, etc.

Assuming the self-check is passed, the system (optionally) will produce one or more appropriate alerts from the Alert Set at step 106 (display of information, current system status, etc.) The user optionally may be given an opportunity to change system settings or review parameters at step 114, including, e.g., changing the time, altering the alarm time, setting alarm preferences, or reviewing sleep parameters obtained previously by the device. Preferably this opportunity to change or review parameters would time out after a preset length of time.

The system then determines if the user is in bed at step 116 using in-bed sensing. The in-bed sensing can be an RF transmitter/receiver pair that passively senses if the user is in bed, or a manual button press on the device used by the user to indicate same. The preferred method is passive RF. If the user is in bed, the system starts the In Bed Mode at 118 in FIG. 2B, transferring control to step 120, as described below. If the user is not in bed then the system starts the Out of Bed Monitor Mode at 190 in FIG. 2C transferring control to step 192.

In Bed Mode

When the system enters the In Bed Mode (FIG. 2B), preferably it will produce a brief audible or tactile alert (depending on the user preferences) in the form of an audible chirp or short vibratory action and produce a stimulus control or other instruction such as "Try to sleep now. Do not do any other tasks such as work or reading," or other stimulus control or sleep hygiene messages. Then, at step 120, several variables are initialized: variable T is set to zero, TBonus is set to zero, and the Maintenance flag is set to FALSE. A separate subsystem preferably continuously determines wake/sleep status, in-bed status and keeps track of the current elapsed time.

TBonus and the Maintenance flag are used to implement the basic rules outlined above. TBonus is used in particular to implement the Special Rules as described earlier. Special Rule #2 is intended to provide the user with extra time to fall asleep during the sleep onset period if they already achieved a brief interval of sleep between 5-10 minutes. The Special Rules are not formally part of the conventional stimulus control instructions, but were thought to be helpful given the rigid nature of machine-implemented rules. The Maintenance flag is used to indicate when the user has left the sleep onset period (because of sleeping at least 10 minutes). This allows the device to follow the maintenance rules and ignore the sleep onset rules.

The system then proceeds to step 122, as it waits for a new wake/sleep determination to be generated after a sufficient amount of EEG data has been collected (an epoch of data). For the purposes of this preferred embodiment of the invention, an epoch length of 30 seconds is deemed adequate.

When an epoch of data has been collected and a wake/sleep determination has been made, or the in-bed sensor changes status (either through the automatic means described below or by a manual indication by the user), or the current time exceeds the preset wake time, then variable T is set to the current elapsed time and the system proceeds to step 124. Here, the system determines if the user is in bed: if the user is not in bed then the system proceeds to transfer control to the Out of Bed Monitor Mode at 126 in FIG. 2C; if the user is in bed, then the system checks to see if it is time to wake the user (optional alarm clock function) at 128. If it is time to wake the user, then the system transfers control to the Wake Mode at 160 in FIG. 2D. If it is not time to wake the user, then the system checks the user's EEG wake/sleep status: if the user is not awake, then the system at 134 transfers to step 136. At step 136, the system checks the user's wake/sleep history to see if, during the last 10 minutes, the user was asleep. If they were, then the Maintenance flag is set at 138 to TRUE and the system returns to a wait condition at 122. Otherwise, the system returns to 122 without changing the Maintenance flag. If the user is now awake (i.e. the most recent wake/sleep determination is wake), then at 134 the system transfers to step 140 in which it is checked as to whether the last two wake/sleep determinations were both awake (i.e., this epoch and the one immediately preceding). If at 140 there is an indication that the user has not been awake for both epochs (i.e., has just woken up), then a check is run at 142 of the wake/sleep history to see if, during the last 5 minutes, the user was asleep. If this shows that the user was not asleep for at least the last 5 minutes, then the system returns to a wait condition at step 122. Otherwise the system checks at 144 to see if TBonus was previously set. If TBonus was not previously set, that is TBonus equals zero, then at 146 the system sets TBonus to the current elapsed time plus 10 minutes and returns to 122. This will effectively inhibit the alarm for 10 minutes as a reward for at least 5 minutes of contiguous sleep during the sleep onset period. If a determination is made that TBonus was previously set, that is, TBonus is not equal to zero, then the system returns to 122 (i.e., don't give a second bonus).

If the indication at 140 is that the user was awake for both epochs, then a check is made at 143 to see if the Maintenance flag is TRUE. If it is TRUE, then a check is made at 145 of the wake/sleep history to see if, during the last 15 minutes, the user was awake for at least 14 minutes. If the user was not awake for at least 14 of the past 15 minutes, then the system returns to 122. Otherwise, control is transferred to the Alert Mode at 220 in FIG. 2E. If the Maintenance flag is not TRUE, then at 150 the system checks to determine whether the variable T is greater than or equal to 20 minutes (length of the sleep onset period) AND that the variable T is greater than or equal to TBonus. If they are both TRUE, then the system transfers control to the Alert Mode at 220 in FIG. 2E. Otherwise, the system returns to a wait condition at 122.

Wake Mode

Figure 2C:
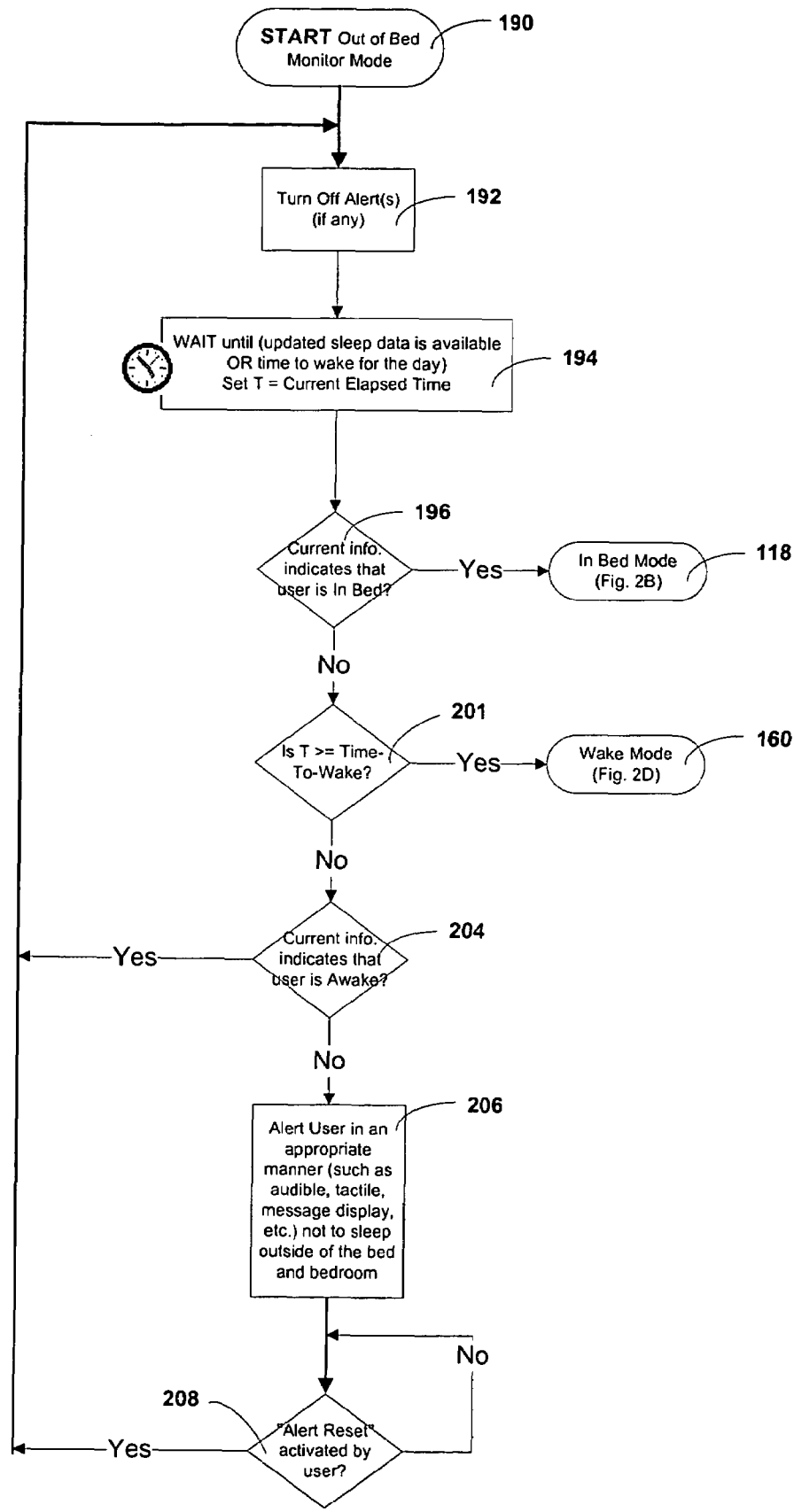
Figure 2D:
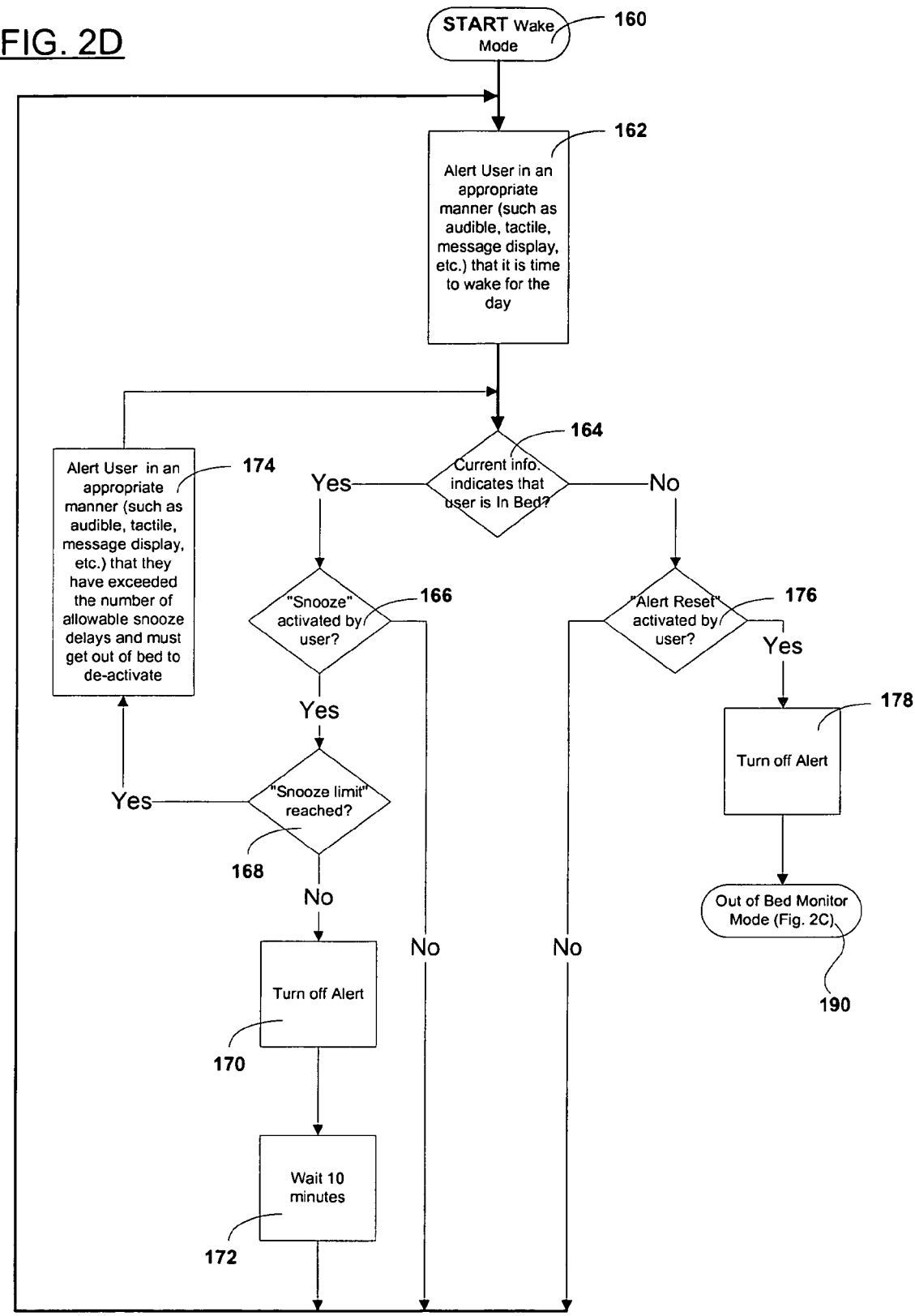

In the Wake Mode at 160 in FIG. 2D, the system alerts the user to wake for the day and get out of bed at step 162 in an appropriate manner. Depending on user preferences, the alert may be any one of the alerts in the Alert Set. An in-bed sensor at step 164 determines the location of the user. If the user is in bed, then the alert continues until the user activates the "snooze" function at 166 (similar to a standard alarm clock with snooze function). If the user activates the snooze function 166 and has not exceeded a preset snooze time limit 168 (i.e., do not allow the user to press the snooze indefinitely), then this would deactivate the alert at 170 for 10 minutes as indicated at 172, after which the alert would resume at 162. If the snooze limit was reached or exceeded, then an appropriate alert would be generated at 174, and the system returns to 164. While proper sleep hygiene would have the user leave the bed at their scheduled wake time, the optional addition of a snooze function is felt to make the device more likely to be used. The snooze limit helps ensure that the user does not stay in bed for an exceedingly long time. The alert can only be deactivated by the user leaving the bed as indicated at 164 and using the Alert Reset function 176. When the user is out of bed and activates the Alert Reset at 176, then the Alert is turned off at 178; otherwise, the alarm continues (back to 162). Following Alert deactivation, at 180 the system transfers control to the Monitor Mode at 190 in FIG. 2C.

Out of Bed Monitor Mode

When the system enters the Out of Bed Mode at 190 in FIG. 2C, it may produce a brief audible or tactile alert (depending on user preferences) in the form of an audible chirp or short vibratory action and produces a stimulus control or other instruction such as "Go back to bed only when you feel tired and want to try sleeping again" and/or "do not sleep while out of bed." At 192 all alerts (if any) are deactivated. The system waits for a new wake/sleep determination to be generated after a sufficient amount of EEG data has been collected (called an epoch of data), and then the variable T is set to the current elapsed time at step 194. For the purposes of the currently preferred embodiment, an epoch length of 30 seconds is deemed adequate. A separate subsystem (hardware and/or software) continuously determines wake/sleep status, in-bed status and keeps track of the current elapsed time. When an epoch of data has been collected and a wake/sleep determination has been made, or the in-bed sensor changes status (either through the automatic means previously described or by a manual indication by the user), or the current time exceeds the preset wake time, then variable T is set to the current elapsed time and the system proceeds to determine if the user is in bed or not (as described previously) at 196. If the user is in bed then the system proceeds to step 198 which transfers control to the In Bed Mode at 118 in FIG. 2B. If the user is not in bed, then the system checks to see if it is time to alert the user that they have reached their wake time (alarm clock function) at 201. If it is time to wake the user, then control is transferred to the Wake Mode at 160 in FIG. 2D. If it is not time to alert the user, then the system checks the wake/sleep decision status at 204. If the user is awake (i.e. the most recent wake/sleep determination is wake), then at 204 the system transfers back to step 192 and continues to passively monitor the user. If the system indicates at 204 that the user is not awake (i.e. they are now asleep) then the user is sleeping while not in bed, which is contraindicated behavior. In this situation, an appropriate alert is produced at 206 to both wake the user and indicate to them (e.g. using text instructions) that they should not sleep while not in bed. Depending on user preferences, the alert can be chosen from the Alert Set. Once the alert has been generated at 206, the alert would continue until the user activates the Alert Reset function at 208. When the Alert Reset is activated, then the alert is turned off and monitoring continues at 192.

Alert Mode

Figure 2E:
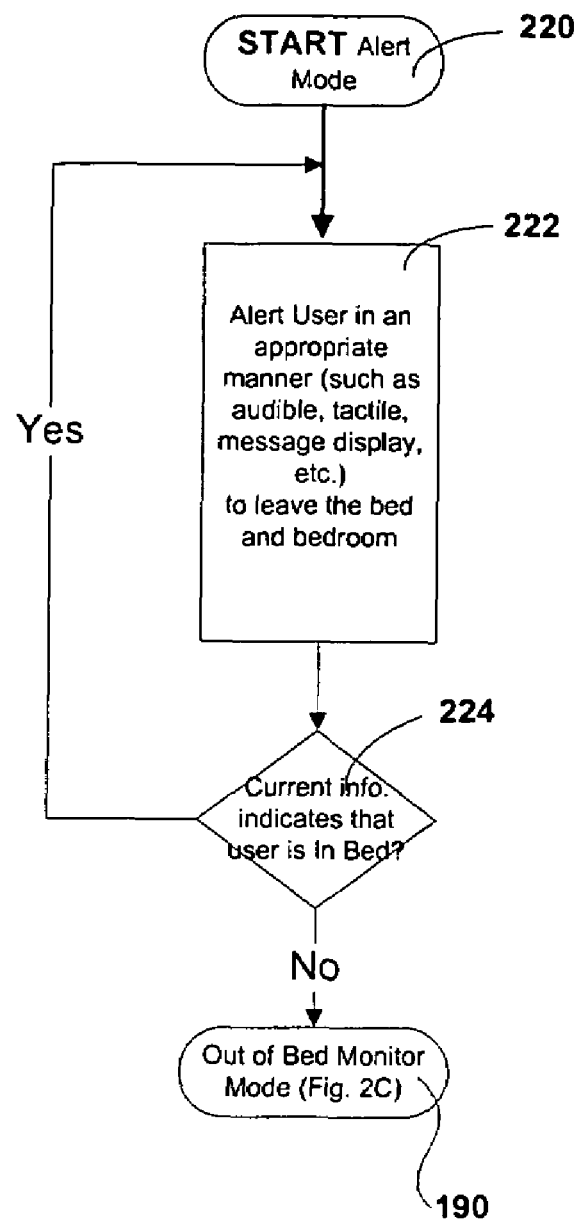

When the systems enters Alert Mode at 220 in FIG. 2E, the system alerts the user in an appropriate manner that they should leave the bed and bedroom at step 222. Depending on user preferences, the alert would most likely involve a text message display, activation of the display backlight, an audible indication, a tactile indication or any of the other alerts of the Alert Set. The alarm would continue until the user gets out of bed at 224 as determined by the in-bed sensor (described previously). After the user gets out of bed, the system transfers control at 226 to the Out of Bed Monitor Mode at 190 of FIG. 2C.

Optional Features

It should be noted that the following features of the system depicted in FIGS. 2A-2E are optional:

1. A wake up feature to allow the user to specify a wake up time and act as an alarm clock to wake the user at a consistent time each morning. If such a feature is present, the user should have the ability to enable/disable or to specify a new time as needed.

2. An out of bed monitor which, when the user leaves the bed, monitors them for sleep outside of the bed and bedroom. This would help prevent napping which could adversely affect their insomnia treatment.

3. A display which, whenever the user is out of bed, displays data and summary statistics for the current recording period. For example, if the user gets out of bed in the middle of the night for some reason, the device may display the number of hours they have been asleep, the number of hours they have been in bed, their sleep efficiency so far this night, the current or elapsed time, etc.

4. An alert to get out of bed may be maintained until the user actually gets out of bed. In the absence of an automatic in-bed sensor, the user would have to indicate to the device that they are out of bed (i.e. button press) to stop the alert.

5. The presentation of (context sensitive) instructions and information on an appropriate monitor or by prerecorded or synthesized voice. For example, when the user is in bed and the device tells them to leave the bed, it would give appropriate instructions such as "leave the bed and bedroom, only return when ready to try to sleep". Or, when the user is out of the bed, it could tell them to "return/go to bed only when sleepy and ready to try to sleep". Or, when they first get into bed, it could tell them to "try to go directly to sleep, no reading or TV, turn the lights out", etc.

Application to Sleep Restriction Therapy

Figure 3:
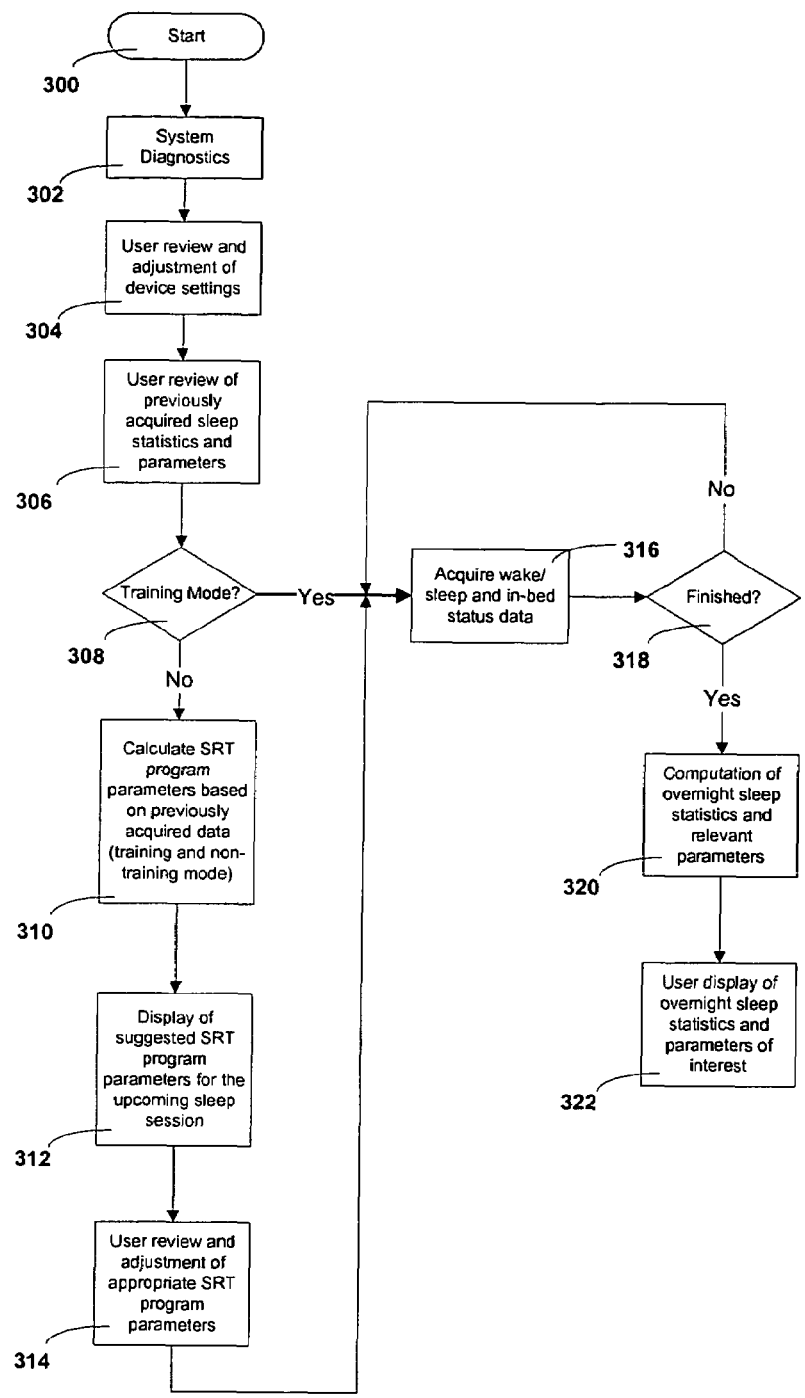
FIG. 3 is a flowchart presenting a high level overview of an automated implementation of sleep restriction therapy in accordance with the present invention.

FIG. 3 represents a high level overview of an implementation of sleep restriction therapy in an automated device, in accordance with the present invention.

The system starts with power-on or connection of EEG electrodes 300. The system completes a diagnostic procedure 302 that may include: hardware, software, power, electrode/sensor status, etc. Errors and warnings should be handled as appropriate. Following diagnostics, there should be an opportunity for the user to make adjustments to system settings at 304. On the first use of the device, these settings may be displayed for review by default. On subsequent use of the device, this menu may be optionally displayed or called up by the user. These settings will include such items as setting the current time, age, sleep goals, alert preferences (audible, tactile or both), language, setup parameters, display preferences, backlight preferences, use of abbreviated messages, use of verbose messages, etc. Each time the device is started (or the user is connected, etc.) the system may display individual night or summary statistics and allow the use to review them as desired. Progress trends, etc. may also be displayed at 306. This all falls under the category of user feedback.

The system will need to acquire sleep related parameters from the user for a number of nights before implementing the sleep restriction therapy program. Most experts currently use one week of data to determine the program parameters. In order to eliminate alteration of sleep due to the addition of this device, the first day or two of data may be eliminated from the calculation of program parameters. The system could automatically start in training mode or the user could select training mode manually. If the system is in training mode 308, then the system will acquire wake/sleep data, the in-bed status (either derived manually or using automatic means), the time of each observation, etc. at 316. These observations could be made every 30 seconds or at other desired intervals. When the night's data collection is finished at 318, the recording will stop. The system will know that the recording is finished either by the user manually indicating such to the device or when the electrodes/sensor is disconnected. When the data collection is completed, the system will compute the necessary sleep related parameters 320 and display them to the user 322. Parameters relevant to the sleep restriction therapy program will be computed, such as total time asleep, total time in bed, sleep efficiency, etc.

If the system is no longer in training mode, at 308 it will transfer to 310 where the sleep restriction therapy program parameters will be computed based on previously collected data. Parameters such as average number of hours asleep over the past week and average sleep efficiency over the past week will be calculated. The sleep restriction therapy program parameters will be displayed to the user at 312. The user may have the opportunity to change certain program parameters at 314, after which the system will continue at step 316 forward. The data collected each night (which could be collected at step 316) would look similar to:

TABLE 2

| | Sleep History | | | | | | | |
|---|---|---|---|---|---|---|---|---|
| Time | 0 | 30 | 60 | 90 | ... | 25200 | 25230 | 26000 |
| Awake? | 1 | 1 | 1 | 1 | ... | 0 | 0 | 0 |
| Inbed? | 0 | 0 | 0 | 1 | ... | 1 | 1 | 1 |

Time: elapsed time in seconds
Awake: determined periodically by the wake/sleep determination means
In-bed: determined by the in-bed sensor or user indicated The memory required to store the data of Table 2 is minimal. If we assume a new set of values every 30 seconds, and use a 4 byte long integer to store the time and a 1 byte number to store the awake and in-bed results, this would result in 12 bytes/minute. At this rate, 1 megabyte of memory or other storage device could hold over 180 nights of sleep history data, or over 60 days of continuous recording.

In the above sleep restriction therapy example, the user started awake and out of bed and finished asleep and in-bed. As the system runs during the sleep period, new sleep history values are added to the table (either in memory or in a storage device). Any of the behavioral therapies implemented using the present invention, as well as several of the sleep hygiene rules, can make use of the sleep history information.

The above sleep history data is sufficient to calculate the sleep restriction therapy program parameters and allow the user to track their progress toward helping their symptoms of insomnia.

The system depicted in FIG. 3 may also include optional features as follows:

1. A step in which additional information related to the time interval(s) corresponding to the highest likelihood of sleeping is calculated. For example, consider a user that averages 5 hours of sleep per night, where sleep is concentrated between the hours of 3 to 6 AM on the majority of nights (this is the time interval when the user was most often asleep). The "standard" implementation of the sleep restriction therapy program would simply suggest that the user limit their time in bed to 5 hours per night. With this additional information, the device used to implement the system could further suggest that they plan their 5 hours of sleep to coincide with the hours of 3-6 AM to further increase their chances of sleep.

2. Going a step further, the device could trigger an alert when the user is getting close to this optimal time for sleeping. Obviously, the alarm would be inhibited if the user were already in bed.

3. The system could alert the user once they have been in bed for the recommended length of time. In this example, the device would alert the user after they have been in bed for 5 hours.

4. The system may include appropriate means to allow the user to specify a wake up time and act as an alarm clock to wake the user at a consistent time each morning. The user should have to ability the enable/disable or specify a new time as needed.

5. The user could wear the device when out of bed and the device could monitor them for sleep outside of the bed and bedroom. This would help prevent napping which could adversely affect their insomnia treatment.

6. Whenever the user is out of bed, the device may display data and summary statistics for the current recording period. For example, if the user gets out of bed in the middle of the night for some reason, the device may display the number of hours they have been asleep, the number of hours they have been in bed, their sleep efficiency so far this night, the current or elapsed time, etc.

Implementation

Implementation of the system of the invention with any behavioral insomnia therapy begins with the physical arrangement of the hardware of the passive monitoring modality to be used. Table 3 below identifies wake/sleep determination means, which may be used with the present invention. Use of any of the passive monitoring modalities described in Table 3 should be performed in accordance with the device specifications.

TABLE 3

Passive Monitoring Modalities*

| Modality | Attachment to User |
| --- | --- |
| EEG | (1) Electrodes located on the head, ideally located outside of the hairline to facilitate self application<br>(2) Ideally use pre-gelled self-stick electrodes<br>(3) Could also ensure electrode attachment using a mechanical fastener such as a headband |
| EMG | (1) Electrodes located at appropriate sites, preferably in a location that would be compatible with sleep<br>(2) Ideally use pre-gelled self-stick electrodes<br>(3) Could also ensure electrode attachment using a mechanical fastener |
| Actigraphy (activity or movement monitor) | (1) Could be worn on wrist, arm, ankle, leg, or otherwise body mounted as specified by the device |
| Body movement sensor(s) | (1) Could be a contact device attached to the wearer according to the specifications of the device<br>(2) Could be a non-contact device mounted on the bed or stationary object (pressure sensors, movement sensors)<br>(3) Could be a non-contact passive device (RF motion detector, ultrasonic motion detector, machine vision system to detect motion/movement) |
| Galvanic skin response | (1) Attached to a convenient location on the skin that is compatible with sleeping |
| Respiratory responses | (1) Could use respiratory belts/bands<br>(2) Flow monitors (oral or nasal thermisters)<br>(3) Monitor breathing sounds using a contact or non-contact microphone |

TABLE 3-continued

Passive Monitoring Modalities*

| Modality | Attachment to User |
| --- | --- |
| EOG | (1) Electrodes to monitor eye movements can be mounted above and below the eyes or on the sides |
| Eye Movements (non-EOG) | (1) IR and/or microwave reflectance<br>(2) Machine vision system to watch the eyes (camera) |
| EKG (peripheral arterial tone/systolic upstroke times) | (1) Could use electrode locations on the chest to acquire the EKG<br>(2) Could use electrode locations on extremities (i.e., one on each wrist) to acquire the EKG)<br>(3) Could use an appropriate sensor to get peripheral arterial tone on an extremity<br>(4) Could use a pulse-oximeter to get systolic upstroke times |
| Pulse oximetry | Finger, toe, earlobes or other appropriate locations. |

Thus, for example, in the case of the body worn EEG device, the patient would mount the device as appropriate to their body and attach the electrodes on the head, preferably outside the hairline using pre-gelled self-stick electrodes. Then, if for example, stimulus control therapy was selected (either manually selected by the user or automatically selected by the device), the user would go to bed when ready to try to sleep. The device would know that the user was in bed either through automatic sensing means or by the user indicating this to the device by a button press (or by connection of the electrode cable to a stationary unit).

The system then monitors the user and continuously tracks whether the user is awake or asleep by analyzing their EEG signals. Using this information, the device would follow the algorithmic flow indicated in FIGS. 1 and 2A-2E as discussed above. If the user fell asleep within the appropriate period of time and for at least the prescribed length of time, the device simply continues passive monitoring, while continuously collecting wake/sleep information, in-bed status and time, etc. If the behavioral treatment program dictates that the user should get out of bed, then the device alerts the user through an alarm chosen from the Alert Set. Preferably, the alarm type and intensity would be preset by the user if the default values were not desirable. For example, someone using this device with a bed partner in close proximity may prefer a silent tactile alarm rather than an auditory alarm.

In response to the alert, the user would get out of bed and leave the bedroom until ready to sleep once again (as specified by the stimulus control program of the automated system). If the user remains in bed or does not leave the bedroom, the device would detect this behavior and alert the user that they are not following the program as intended. For those people whose living conditions or situation are such that leaving the bedroom is not feasible, the device could be set to relax this condition. When the user is ready to sleep once again according to the rules of the program (which may be written, but may also be displayed on the device display at the appropriate times or provided verbally), they would once again get back in bed and try to sleep. The unit would monitor continuously, whether in-bed or out of bed. If the unit detected sleep while the user was out of bed, then it would alert the user that this behavior is contraindicated and may reduce the effectiveness of the program. Sleep should be in the bed and bedroom only whenever possible. Since this behavioral therapy is a "reconditioning" program, the rules should be enforced whenever possible. Furthermore, the system would detect any awakenings and, if necessary, alert the user that they need to get out of bed.

As explained earlier, in the case of stimulus control therapy, the user should only be in bed when trying to sleep. When they cannot sleep, they are instructed by the system to physically remove themselves from the bed and bedroom. This would necessitate the device knowing when the user was in the bed. A pressure transducer or motion sensor under the bed sheets could be used to sense whether the user was in bed (and presumably trying to sleep) or not. Or, the user could manually indicate to the device that they were ready to try and sleep by pressing a button on the device (the manual approach). This manual approach suffers from the possibility of the user forgetting to press the button and the device remaining inactive. If the device was body worn, then it could contain an RF receiver that picks up a very low power RF transmitted signal (beacon) placed in close proximity to their bed. The idea being, that when the user is in bed, they would be close enough for the body worn device to detect the low power transmitted signal (beacon) and automatically know that the user was in bed. Many other devices could also be used, such as temperature sensors to pick up body heat, etc. At present, however, a small RF transmitter is preferred, either placed directly under the bed, on the headboard, or on the nightstand and would not be prone to the false detection of a bed partner, pet, etc.

Passive sensors used to determine whether the user is in bed or not, such as a low power RF transmitter, could also be used to help ensure program compliance. In one mode of the invention, when the device alerts the user that they should get out of bed, the alarm (auditory and/or vibratory for example) could continue until the device has detected that the user has physically removed themselves from the bed and bedroom (i.e. out of the transmit range of the beacon). The radiated output of the RF beacon could be directional in nature. Furthermore, the power of the RF beacon could be user adjustable. This would allow the user to adjust the RF beacon so that the transmit pattern was coincident with the bed and bedroom area as much as possible.

Furthermore, the device could help ensure compliance that sleep only occurs in the bed. If a user were to fall asleep on a couch or chair (i.e. not in the bed and bedroom), the device could detect that sleep was occurring outside of the bed and bedroom and signal an alert. Ensuring that sleep occurs only in the bed/bedroom is another step in implementing good sleep hygiene and is part of the overall therapy.

The above illustrates use of the system when only wake and sleep information is available. If additional sleep staging information is available, then it is possible to implement more elaborate schemes. For example, the addition of stage-1 sleep information could enable the system to wake the user from sleep if that user has not progressed beyond stage-1 sleep within a prescribed interval of time (for example, 20 minutes).

Hardware for implementing the inventive system may take many different shapes and forms, such as those described below.

Stationary Devices

A tabletop device for implementing the inventive system could sit on the floor or nightstand next to the user's bed. EEG electrodes (or other appropriate sensors) would connect to a cable that would plug into the device. One disadvantage of this approach is that the user is tethered to a stationary device and it is possible for the wires to tangle or become an annoyance. Routing the wires toward the top of the bed and then to the device usually solves this problem. When the user has to get out of bed (i.e. needs to use the bathroom, or because the device instructs them to do so) then they must disconnect themselves from the stationary device and carry the electrode cable with them. Thus, a benefit of this approach is that the user must reattach themselves to the device when back in bed and this would provide the necessary information for the device to start and stop without any other detectors or actions on the part of the user (i.e. this is essentially an automatic in-bed sensor by default). Finally, the device would not be able to continuously monitor the user when out of bed for any sleep outside of the bed and bedroom. If the tabletop device was powered from the wall outlet, then suitable ground isolation design techniques must be employed to prevent a ground hazard using design techniques well known in the art.

Semi-Stationary

A tabletop model, as described above, but using a wireless connection between the electrodes/EEG amplifiers and the stationary device, may also be used. In this case, the electrodes would plug into a small wireless EEG amplifier/transmitter that can be body worn to send signals to the tabletop device. This has the advantage of removing the tether between the user and a stationary object. It also provides inherent electrical isolation between the user and the device, since the transmitter worn by the user would most likely be battery powered. This also has the advantage of being used as a bed sensor if the transmitter is low power or has the ability to sense the distance from the transmitter to the base unit. If the transmitter is powerful enough, the device may be used for out of bed monitoring as well.

Body Wearable

The most desirable form of the hardware for implementing the present inventive system would have the entire device be body worn. In this case, the device is worn by the user and the electrodes plug directly into the device. The device would most likely be powered by batteries and would not need to be isolated from the wall outlet. This device would be simpler than the semi-stationary system described above since it would not need a sophisticated EEG transmitter/receiver pair. The user would also be untethered at all times, thereby making it preferable to the stationary device as described above. The body wearable device would also be able to monitor the user for out of bed sleep and prevent this from occurring.

This device would likely require a wireless in-bed sensing device, such as a low power RF transmitter mounted near the bed as previously described. The body worn device would simply need to detect the beacon signal. A more sophisticated model would gauge the distance to the transmitter and know whether the user was in bed or just nearby. A pressure sensor under the bed sheet with a very low power RF transmitter optimally could also be used for bed detection. In a simple approach, however, the user may just press a button on the body worn device to indicate that they are in-bed and ready for sleep. Other device embodiments could sense light and movement and actively prompt the user as to whether they are now going to attempt sleep.

Figure 4:
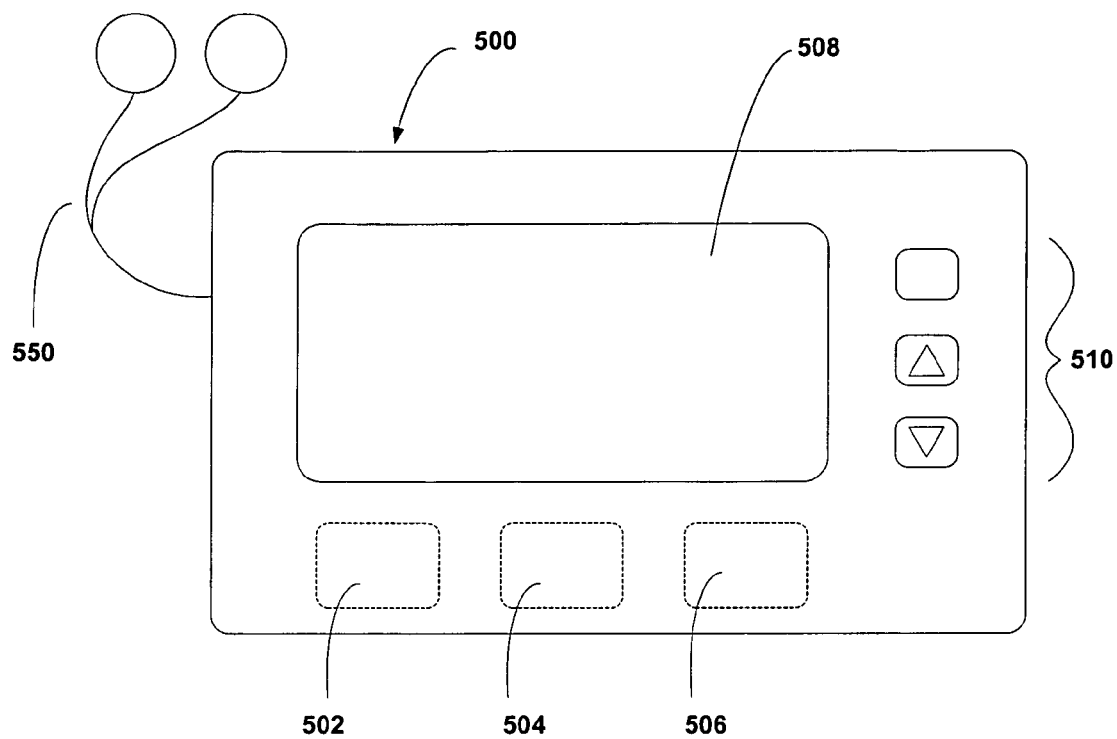
FIG. 4 is a diagrammatic representation of one possible body wearable device in accordance with the present invention.

One possible body wearable device 500 is depicted diagrammatically in FIG. 4. It includes (visual, audible and tactile alerts 502, 504 and 506), an HMI (human machine interface) display 508 (backlit LCD and lights), HMI input 510 (buttons for input and navigation), a power source (not drawn).

Figure 5:
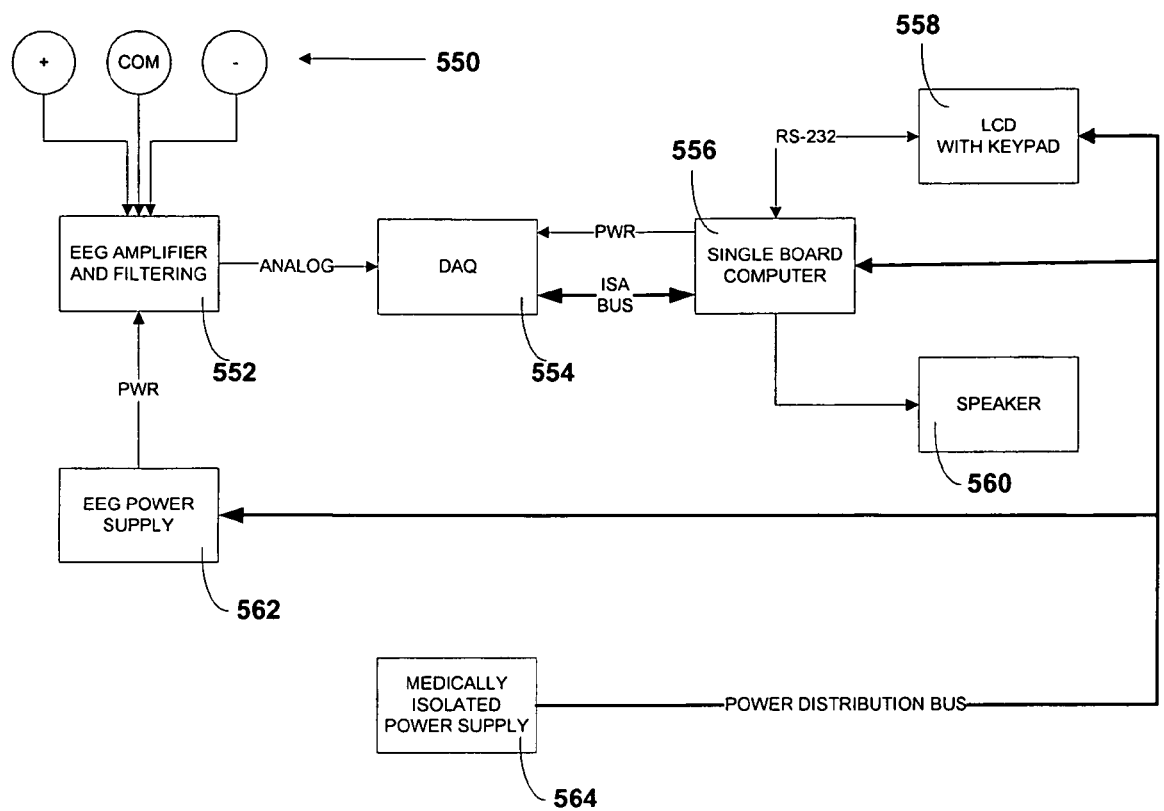
FIG. 5 is a block diagram representation of a stationary EEG based embodiment of the present invention.

An EEG based embodiment of the present system may be implemented using a body wearable device or otherwise, in which electrodes 550 are used as sensors on the person to be monitored, as represented in FIG. 4 and in the block diagram of FIG. 5. The block diagram of FIG. 5 represents the components of an EEG based embodiment of the present system in a stationary design that is capable of implementing wake/sleep determination as specified in U.S. Pat. No. 5,813,993 to the present inventors. While the algorithm described in this patent can be used for wake/sleep determination in the present invention, any other suitable passive wake/sleep determination means or algorithm could also be employed in its place.

Examples of components that could be used in the stationary design of FIG. 5 are described below. One skilled in the art could choose alternate components, while preserving the overall functionality, to build a body wearable design. For example, in such a body wearable design, the single-board computer of 556 could be replaced with a digital signal processor (DSP), etc.

The electrodes 550 of FIG. 5 are attached to the user to acquire their EEG signal. The + and − electrodes are the inputs to the EEG amplifier and the com electrode is used to bring the reference point of the EEG amplifier to the same electrical potential as the user. Many EEG based devices use proprietary electrodes designed specifically for their devices. The following work well: NeoTrace Kitty Cat Electrode, Kendall-LTP part number 1052NPSM, which is a self stick electrode with a solid gel adhesive hydrogel and a preattached lead wire with 1.5 mm safety socket termination.

Electroencephalographic (EEG) amplifier and filtering 552 comprise an integrated EEG amplifier in an OEM module. This module amplifies and filters the EEG signal from electrodes 550. Most amplifier modules contain more than one channel. Depending on the number of channels required by the desired wake/sleep determination means (assuming EEG based), the + and − inputs of each unused amplifier channel should be shorted together and tied to com to prevent the unused channels from introducing noise into the active channels. A suitable amplifier would be the Teledyne Analytical Instruments, model A0401, 4 channel medical signal processing amplifier.

If the output of the EEG amplifiers 552 is an analog signal, then a data acquisition card (DAQ) 554 is needed to digitize the analog output signal. A suitable DAQ would be the Measurement Computing, model PC104-DAS16JR/16, having a PC/104 form factor. Single board computers (SBC) 556 are typically used in embedded applications. In this example, all of the necessary computer hardware is integrated into this device. A suitable SBC is the Advanced Digital Logic, model MSMP5SEV, a complete 166 MHz Pentium system in a PC/104 form factor.

The illustrated system also includes a liquid crystal display (LCD) with keypad. This is used as both an output device (display and backlight) and an input device (keypad) so that the user can interact with this system. A suitable device is the CrystalFonts, model CFA633-TMC-KS, which is a 2 line LCD with backlight, a 5 button keypad and an RS-232 serial interface. The system further includes a speaker 560 as an audio output device. (The characteristics of the speaker would be specified by the manufacturer of the SBC (556) if a speaker was not included.)

In some instances, the main power supply for the system, such as 564, may not produce the necessary voltages to operate the EEG amplifiers. Furthermore, many digital devices are connected to the power supply 564, and these devices tend to introduce a considerable amount of electrical noise into the power system. The EEG amplifiers may need to be isolated from this electrical noise either though filtering or adding a separate power supply for the analog amplifiers. Thus, the system may optimally also include an EEG power supply 562.

The system has a medically isolated power supply 564. This is the main system power supply. Since the system requires a low impedance electrical connection to the user (using the EEG electrodes 550), it is advisable to use a medically isolated power supply. A suitable power supply is the Integrated Power Designs, model SRP-35A-1002, which provides medically isolated 5VDC at 35 Watts.

Finally, it is noted that a body wearable device would be functionally similar to that of the system of FIG. 5, but with different miniaturized hardware. Also, a body wearable system may also include a vibrating alert and would be battery operated. It may also include an in-bed sensor.

While the present invention has been described in relation to preferred embodiments, those skilled in the art may develop variations in the details thereof without departing from the principles of the invention. Accordingly, the appended claims are intended to be construed to cover all equivalents falling within the scope and spirit of the invention.

What we claim is:

1. An automated system for facilitating the implementation of behavioral therapy that uses information indicative of a subject's wake/sleep state to treat subjects suffering from insomnia including difficulty falling asleep, difficulty staying asleep, or waking too early, comprising:
   passive wake/sleep determination means for producing information indicative of the subject's wake/sleep state; and
   means for implementing the behavioral therapy utilizing the wake/sleep information to treat the subjects suffering from insomnia chosen from the group consisting of stimulus control therapy, sleep restriction therapy, relaxation therapy, and combinations of two or more of stimulus control therapy, sleep restriction therapy, or relaxation training.

2. The system of claim 1 including means for choosing the behavioral therapy to be implemented for a subject based on the subject's personal wake/sleep information.

3. The system of claim 2 including means for obtaining information indicative of the subject's wake/sleep state prior to the beginning of treatment.

4. The system of claim 2 including means for obtaining information indicative of the subject's wake/sleep state during the course of treatment.

5. The system of claim 1 in which the passive wake/sleep determination means uses information taken from the group consisting of:
   EEG, EKG, EMG, EOG, actigraphy, body movement, galvanic skin response, respiratory changes, or eye movements, and combinations of two or more of EEG, EKG, EMG, EOG, actigraphy, body movement, galvanic skin response, respiratory changes, or eye movements.

6. The apparatus of claim 5 including means for permitting the subject to review and adjust system settings chosen from the group consisting of time, age, sleep goals, alert preferences, language, setup parameters, and display preferences.

7. The system of claim 1 including drug therapy in conjunction with the behavioral therapy.

8. The system of claim 1 in which active means for determining the wake/sleep state are used to supplement the passive wake/sleep determination means.

9. The system of claim 1 in which the behavioral therapy is stimulus control therapy including means for implementing the stimulus control therapy using the following rules:

a) never alert a subject while they are asleep
b) alert a subject only when at least a first predetermined number of contiguous of wake epochs are achieved, and
c) if any sleep of at least a second predetermined number of contiguous epochs is achieved, designate the subject in a sleep maintenance mode and if any sleep of at least the second predetermined number of contiguous epochs is not achieved, designated the subject not in a sleep maintenance mode whereby if the subject is in a sleep maintenance mode, examine a past third predetermined number of epochs and if the subject was awake for at least a fourth predetermined number of epochs out of the past third predetermined number of epochs, alert the subject, but if the subject is not in a sleep maintenance mode and if there is no sleep of at least a fifth predetermined number of contiguous epochs within a first period of trying to fall asleep, then alert the subject upon a lapse of the first period; and if the subject is not in a sleep maintenance mode and there is a contiguous sleep period contained within the first period of trying to fall asleep that is greater than or equal to the fifth predetermined number of epochs but less than the second predetermined number of epochs, then inhibit the alert for an additional period.

10. The system of claim 9 in which an epoch is about 30 seconds, the first predetermined number of contiguous wake epochs is 2, and the second predetermined number of contiguous epochs is 20 epochs, the third predetermined number of epochs is 30 epochs, the fourth predetermined number of epochs is 28 epochs; the fifth predetermined number of contiguous epochs is 10 epochs; the first period is 40 epochs, and the additional period is 20 epochs.

11. The system of claim 1 in which the behavioral therapy is optimized for each subject based upon the subject's wake/sleep information.

12. The system of claim 1 in which behavioral prompts in the form of alerts or messages are generated in accordance with the behavioral therapy being implemented.

13. The system of claim 1 in which the subject's wake/sleep states, in-bed status, and other sleep behaviors are stored and used to update the parameters for the behavioral therapy being implemented.

14. An apparatus for facilitation the implementation of behavioral therapy for treating subjects suffering from insomnia including difficulty falling asleep, difficulty staying asleep, or waking too early, comprising:
means for processing information taken form the group consisting of: EEG, EKG, EMG, EOG, actigraphy, body movement, galvanic skin response, respiratory changes, eye movements and combinations of two or more thereof to determine the subject's wake/sleep state; and
means for implementing the behavioral therapy utilizing the wake/sleep state information to treat the subjects suffering from insomnia chosen from the group consisting of stimulus control therapy, sleep restriction therapy, relaxation therapy, and combinations of two or more of stimulus control therapy, sleep restriction therapy, or relaxation training.

15. The apparatus of claim 14 in which the behavioral therapy is stimulus control therapy in which program parameters are defined and stimulus control therapy rules are applied to implement the therapy comprising:
means for determining whether the subject should get out of the bed in accordance with the stimulus control therapy; and
means for alerting the subject to leave the bed in accordance with the rules of the stimulus control therapy if a determination is made.

16. The apparatus of claim 15 in which the alerting means are chosen from the group consisting of: a text display of warning conditions, text display of instructions or information, a display backlight, a blinking light, an audible indication, a tactile indication, a synthesized or recorded voice, a low level electrical stimulus and an aroma generated by appropriate device.

17. The apparatus of claim 15 including subject-controlled means for canceling the alerting means.

18. The apparatus of claim 14 in which the behavioral therapy is sleep restriction therapy in which program parameters are defined and sleep restriction therapy rules are applied to implement the therapy comprising:
means for calculating the program parameters including a sleep period for the upcoming sleep session based on previously acquired wake/sleep state information in accordance with the rules of the sleep restriction therapy;
means for determining whether the subject has completed the sleep period; and
means for displaying the calculated program parameters to the subject for the upcoming sleep session.

19. The apparatus of claim 18 including means for enabling the subject to review and adjust the program parameters after display of such parameters for an upcoming sleep session.

20. The apparatus of claim 14 in which the behavioral therapy is chosen from the group consisting of stimulus control therapy, sleep restriction therapy, relaxation therapy, and combinations of two or more of stimulus control therapy, sleep restriction therapy, or relaxation training.

21. The apparatus of claim 14 in which the behavioral therapy is optimized for each subject based upon the subject's wake/sleep state information and/or wake/sleep state history.

22. The apparatus of claim 14 including means permitting the subject to review information previously acquired by the apparatus.

23. The apparatus of claim 14 including means for computing the subject's sleep statistics based on the subject's previous wake/sleep state history.

24. The apparatus of claim 14 in which information as to whether the subject is in bed or not is acquired along with the wake/sleep state information.

25. The apparatus of claim 24 in which means are provided fro the turning off any alert and displaying the subject's current sleep statistics when a determination is made that the subject is no longer in bed.

26. The apparatus of claim 24 in which means are provided for the turning off any alert and for providing the subject with sleep instructions when a determination is made that the subject is no longer in bed.

27. The apparatus of claim 14 including means for permitting the subject to specify a predetermined wakeup time.

28. The apparatus of claim 14 including a visual or audible presentation of instructions or information.

29. The apparatus of claim 14 including means for providing an indication to the subject after the subject has been in bed for a recommended length of time.

30. The apparatus of claim 14 in the form of a single portable unit wearable by the subject.

31. The apparatus of claim 14 including means for calculating a time interval corresponding to the highest likelihood of being able to sleep to assist the subject in planning the subject's sleep.

32. The apparatus of claim 31 including means for informing the subject as the subject approaches the time interval corresponding to the highest likelihood of sleeping.

33. An automated system for facilitating the implementation of stimulus control therapy that uses information indicative of a subject's wake/sleep state to improve the subject's sleep or sleep hygiene, including subjects with insomnia or other sleep complaints, comprising:
passive wake/sleep determination means for producing information indicative of the subject's wake/sleep state; and
means for implementing the stimulus control therapy utilizing the wake/sleep information and applying the following rules:
a) never alert a subject while they are asleep,
b) alert a subject only when at least a first predetermined number of contiguous of wake epochs are achieved, and
c) if any sleep of at least a second predetermined number of contiguous epochs is achieved, designate the subject in a sleep maintenance mode and if any sleep of at least the second predetermined number of contiguous epochs is not achieved, designate the subject not in a sleep maintenance mode whereby
if the subject is in a sleep maintenance mode, examine a past third predetermined number of epochs and if the subject was awake for at least a fourth predetermined number of epochs out of the past third predetermined number of epochs, alert the subject, but
if the subject is not in a sleep maintenance mode and if there is no sleep of at least a fifth predetermined number of contiguous epochs within a first period of trying to fall asleep, then alert the subject upon a lapse of the first period; and
if the subject is not in a sleep maintenance mode and there is a contiguous sleep period contained within the first period of trying to fall asleep that is greater than or equal to the fifth predetermined number of epochs but less than the second predetermined number of epochs, then the alert for an additional period.

34. The system of claim 33 in which an epoch is about 30 seconds, the first predetermined number of contiguous wake epochs is 2, and the second predetermined number of contiguous epochs is 20 epochs, the third predetermined number of epochs is 30 epochs, the fourth predetermined number of epochs is 28 epochs; the fifth predetermined number of contiguous epochs is 10 epochs; the first period is 40 epochs, and the additional period is 20 epochs.

35. An automated system for facilitating the implementation of stimulus control therapy that uses information indicative of a subject's wake/sleep state to improve the subject's sleep or sleep hygiene, including subjects with insomnia or other sleep complaints, comprising:
means for processing information taken from the group consisting of: EEG, EKG, EMG, EOG, actigraphy, body movement, galvanic skin response, respiratory changes, eye movements and combinations of two or more thereof to determine the subject's wake/sleep state and to acquire and alert as to whether the subject is in bed or not; and
means for implementing the behavioral therapy utilizing the wake/sleep state information and the in bed information.

36. The apparatus of claim 35 in which means are provided for the turning off any alert and displaying the subject's current sleep statistics when a determination is made that the subject is no longer in bed.

37. The apparatus of claim 35 in which means are provided for the turning off any alert and for providing the subject with sleep instructions when a determination is made that the subject is no longer in bed.

38. An automated system for facilitation the implementation of behavioral therapy that uses information indicative of a subject's wake/sleep state to improve the subject's sleep or sleep hygiene, including subjects with insomnia or other sleep complaints, comprising:
passive wake/sleep determination means for producing information indicative of the subject's wake/sleep state;
means for implementing the behavioral therapy utilizing the wake/sleep information; and
means for storing the subject's wake/sleep states, in-bed status, and other sleep behaviors and using the stored information to update the information for the behavioral therapy being implemented.

* * * * *

UNITED STATES PATENT AND TRADEMARK OFFICE
CERTIFICATE OF CORRECTION

| | | |
|---|---|---|
| PATENT NO. | : 7,654,948 B2 | Page 1 of 1 |
| APPLICATION NO. | : 10/790885 | |
| DATED | : February 2, 2010 | |
| INVENTOR(S) | : Richard Kaplan et al. | |

It is certified that error appears in the above-identified patent and that said Letters Patent is hereby corrected as shown below:

Title page, item [73] Assignee: should read as follows: Consolidated Research of Richmond, Inc.

Signed and Sealed this
Thirty-first Day of January, 2012

David J. Kappos
*Director of the United States Patent and Trademark Office*